(12) United States Patent
Wagner

(10) Patent No.: US 8,946,393 B2
(45) Date of Patent: Feb. 3, 2015

(54) METHODS FOR DIAGNOSING LYME DISEASE

(75) Inventor: Bettina Wagner, Ithaca, NY (US)

(73) Assignee: Cornell University, Ithaca, NY (US)

(*) Notice: Subject to any disclaimer, the term of this patent is extended or adjusted under 35 U.S.C. 154(b) by 44 days.

(21) Appl. No.: 13/876,077

(22) PCT Filed: Sep. 27, 2011

(86) PCT No.: PCT/US2011/053359
§ 371 (c)(1),
(2), (4) Date: Jul. 8, 2013

(87) PCT Pub. No.: WO2012/047607
PCT Pub. Date: Apr. 12, 2012

(65) Prior Publication Data
US 2013/0273572 A1    Oct. 17, 2013

Related U.S. Application Data

(60) Provisional application No. 61/386,694, filed on Sep. 27, 2010.

(51) Int. Cl.
C07K 14/20 (2006.01)
A61K 38/00 (2006.01)
(Continued)

(52) U.S. Cl.
CPC ............ *G01N 33/6854* (2013.01); *C07K 14/20* (2013.01); *G01N 33/56911* (2013.01); *G01N 2333/20* (2013.01)
USPC ................ 530/391.5; 424/234.1; 530/389.5; 530/388.4

(58) Field of Classification Search
CPC .......................... G01N 33/569; C07K 14/20
See application file for complete search history.

(56) References Cited

U.S. PATENT DOCUMENTS 5,582,990 A   12/1996  Bergstrom et al.
5,620,862 A    4/1997  Padula
(Continued)

FOREIGN PATENT DOCUMENTS

CN    1159831    9/1997
WO    9715600    5/1997
(Continued)

OTHER PUBLICATIONS

Magnarelli et al, Serologic diagnosis of canine and equine borreliosis: use of recombinant antigens in enzyme-linked immunosorbent assays, J. Clin. Microbiol., Jan. 1997, pp. 169-173.
(Continued)

*Primary Examiner* — Albert Navarro
*Assistant Examiner* — Ginny Portner
(74) *Attorney, Agent, or Firm* — Hodgson Russ LLP

(57) ABSTRACT

A method for diagnosing Lyme disease status in a mammal is provided. The method entails, in a biological sample obtained or derived from a mammal, determining antibodies to *Borrelia burgdorferi* (*B. burgdorferi*) outer surface proteins (Osp) OspA, OspC, and OspF. Based upon determining the OspA, OspC, and OspF antibodies, the mammal can be diagnosed as vaccinated, not vaccinated, infected or not infected with *B. burgdorferi*. Mammals that have early, intermediate or chronic *B. burgdorferi* infection can also be identified. The method is particularly suited for use with horses and dogs. Isolated or recombinant *B. burgdorferi* antigens and compositions that contain them are also provided.

3 Claims, 9 Drawing Sheets (4) streptavidin-phycoerythrin (PE)

(3) biotinylated anti- species specificAb (2) Abs in sample (1) Recombinant *B. burgdorferi* OspA, OspC and OspF antigens are coupled to fluorescent beads

(51) Int. Cl.
*G01N 33/68* (2006.01)
*G01N 33/569* (2006.01)

(56) References Cited

U.S. PATENT DOCUMENTS

| | | | | |
|---|---|---|---|---|
| 5,777,095 | A | * | 7/1998 | Barbour et al. ............... 536/23.7 |
| 5,853,987 | A | * | 12/1998 | Guo et al. .................... 435/6.11 |
| 5,854,395 | A | * | 12/1998 | Champion et al. ............ 530/350 |
| 6,083,722 | A | | 7/2000 | Bergstrom et al. |
| 6,143,872 | A | * | 11/2000 | Barbour et al. ............... 530/359 |
| 6,248,562 | B1 | | 6/2001 | Dunn et al. ................... 435/69.3 |
| 6,312,915 | B1 | | 11/2001 | Nelson et al. |
| 6,464,985 | B1 | | 10/2002 | Callister et al. |
| 6,486,130 | B1 | * | 11/2002 | Livey et al. ................. 514/44 R |
| 6,610,838 | B1 | * | 8/2003 | Bergstrom ................... 536/23.7 |
| 6,676,942 | B1 | | 1/2004 | Lobet et al. |
| 6,716,574 | B2 | * | 4/2004 | Mathiesen et al. ................ 435/4 |
| 7,008,625 | B2 | * | 3/2006 | Dattwyler et al. ......... 424/192.1 |
| 7,794,727 | B2 | * | 9/2010 | Marconi et al. ............ 424/192.1 |
| 7,887,815 | B2 | | 2/2011 | Dattwyler et al. |
| 2002/0071847 | A1 | | 6/2002 | Sadziene et al. |
| 2003/0134345 | A1 | * | 7/2003 | Brunner ....................... 435/7.32 |
| 2004/0086949 | A1 | * | 5/2004 | Holm et al. .................... 435/7.1 |
| 2005/0058661 | A1 | | 3/2005 | Sykes et al. |
| 2005/0147999 | A1 | | 7/2005 | Choi et al. |
| 2006/0034862 | A1 | * | 2/2006 | Lahdenne et al. ......... 424/190.1 |
| 2006/0194267 | A1 | | 8/2006 | Vojdani |
| 2008/0026009 | A1 | * | 1/2008 | Korshus et al. ............ 424/234.1 |
| 2010/0136039 | A1 | | 6/2010 | Lundberg et al. |
| 2010/0278866 | A1 | | 11/2010 | Barbour et al. |
| 2010/0292096 | A1 | | 11/2010 | Luft et al. |
| 2011/0105355 | A1 | | 5/2011 | Luft et al. |
| 2011/0105825 | A1 | * | 5/2011 | Nayfach-Battilana .......... 600/12 |
| 2013/0085076 | A1 | * | 4/2013 | Douglas et al. .................. 506/9 |

FOREIGN PATENT DOCUMENTS

| | | | | |
|---|---|---|---|---|
| WO | 97/42221 | A1 | 11/1997 | |
| WO | 9900413 | | 1/1999 | |
| WO | 0006745 | | 2/2000 | |
| WO | 0065064 | | 11/2000 | |
| WO | 00/78800 | | * 12/2000 | ............. C07K 14/00 |
| WO | 2004103269 | | 12/2004 | |
| WO | 2006/014292 | A2 | 2/2006 | |
| WO | 2007065098 | | 6/2007 | |
| WO | 2011068844 | | 6/2011 | |
| WO | 2011109440 | | 9/2011 | |

OTHER PUBLICATIONS

Wagner et al, A fluorescent bead-based multiplex assay for the simultaneous detection of antiboies to *B. burgdorferi* outer surface proteins in canine serum, Vet. Immun. and Immunopathology, vol. 140, No. 3, Dec. 10, 2010, pp. 190-198.

ErpY protein, retrieved from EBI accession No. UNIPROT:COR6G3, www.uniprot.org/uniprot/C0R6G3, May 5, 2009.

Goettner et al., P28: A multiplex fluorescent particle immunoassay for serodiagnosis of infections with *Borrelia burgdorferi*, X International Jena Symposum on Tick-Borne Diseases, Jan. 2009, p. 106.

Aguero-Rosenfeld et al, Diagnosis of Lyme Borreliosis, Clin. Microbiol. Rev., vol. 18, No. 3, Jul. 2005, pp. 484-509.

Wagner et al, Antibodies to Borrelia burgdorferi OspA, OspC, OspF, and C6 Antigens as Markers for Early and Late Infection in Dogs, Clin. Vaccine Immunol., vol. 19, No. 4, Apr. 2012, pp. 527-535.

Wagner et al, Development of a multiplex assay for the detection of antibodies to *Borrelia burgdorferi* in horses and its validation using Bayesian and conventional statistical methods, Vet. Immunol. and Immunopathol., vol. 144, No. 3-4, Aug. 17, 2011, pp. 374-381.

Magnarelli, L.A., et al., Use of recombinant antigens of *Borrelia burgdorferi* in serologic tests for diagnosis of lyme borreliosis, J. Clin. Microbiol., Feb. 1996, vol. 34, No. 2, pp. 237-240.

Magnarelli, L.A., et al., Serologic Diagnosis of Lyme Borreliosis by Using Enzyme-Linked Immunosorbent Assays with Recombinant Antigens, J. Clin. Microbiol., May 2000, vol. 38, No. 5, pp. 1735-1739.

Gomes-Solecki, M., et al., Recombinant Assay for Serodiagnosis of Lyme Disease Regardless of OspA Vaccination Status, J. Clin. Microbiol., Jan. 2002, vol. 40, No. 1, pp. 293-297.

Rockland Immunochemicals, News and Posters: Multiplex Assay for Lyme Disease [online], Aug. 2, 2010, Available on the internet: web.archive.org/web/20100802110310/www.rockland-inc.com/Support/Newsletters.aspx> and rockland-inc.com/uploadedFiles/Support/Poster%20on%20LymeDisease_Phase1.pdf>.

Elshal, M., et al., Multiplex Bead Array Assays: Performance Evaluation and Comparison of Sensitivity to Elisa, Methods, Apr. 2006, vol. 38, No. 4, pp. 317-323.

* cited by examiner (4) streptavidin-phycoerythrin (PE)

(3) biotinylated anti- species specificAb (2) Abs in sample (1) Recombinant *B. burgdorferi* OspA, OspC and OspF antigens are coupled to fluorescent beads

US 8,946,393 B2

METHODS FOR DIAGNOSING LYME DISEASE

CROSS-REFERENCE TO RELATED APPLICATIONS

This application claims priority to U.S. Provisional Patent Application No. 61/386,694, filed on Sep. 27, 2010, the disclosure of which is incorporated herein by reference.

FIELD OF THE INVENTION

The present invention relates generally to diagnosis of Lyme disease, and more particularly to determining various stages of Lyme disease in mammals, such as equines and canines.

BACKGROUND OF THE INVENTION

Lyme disease is caused by infection with spirochetes of the *Borrelia burgdorferi* sensu lato group. It is a zoonotic disease affecting humans, dogs, horses and other mammalian species. The bacteria are transmitted to the mammalian hosts by infected ticks (*Ixodes* spp.). Lyme disease is the most common vector-borne disease in the United States, Europe and Asia. In Europe and Asia the disease is commonly caused by *B. garinii* and *B. afzelii*, while in the United States *B. burgdorferi* sensu stricto strains are present. In current methods for diagnosis of Lyme disease, serum antibodies to whole *B. burgdorferi* lysates or to individual antigens of the spirochete are commonly analyzed to identify dogs and horses that were exposed to the pathogen and are at risk of developing disease. In dogs and horses, the detection of serum antibodies to *B. burgdorferi* can be performed by ELISA followed by Western blotting (WB), which is an inadequate procedure that is nevertheless still considered the gold standard for human Lyme disease diagnostics. While certain tests are available (such as snap tests for detecting the invariable domain IR6 of the variable surface antigen VlsE of *B. burgdorferi* for dogs and horses), they lack a desirable level of sensitivity and cannot distinguish between various stages of the disease. Thus, there is an ongoing and unmet need for improved methods for diagnosing Lyme disease in mammals, including but not necessarily limited to horses and dogs. The present invention meets these and other needs.

SUMMARY OF THE INVENTION

The present invention provides a method for diagnosing Lyme disease status in a mammal. The method comprises, in a biological sample obtained or derived from the mammal, determining presence or absence of antibodies to *Borrelia burgdorferi* (*B. burgdorferi*) outer surface proteins (Osp) OspA, OspC, and OspF, and based on the presence or absence of the antibodies, identifying the mammal as infected or not infected with *B. burgdorferi*. The method includes determining whether or not the animal has been vaccinated against *B. burgdorferi*. The method permits discriminating between various stages of Lyme disease, i.e., early, intermediate or chronic *B. burgdorferi* infection, based on the determining the presence or the absence of the antibodies. In one embodiment, the mammal is identified as not infected with *B. burgdorferi* by determining an absence of the antibodies to the OspA, OspC and OspF antigens. In one embodiment, the only antibodies to *B. burgdorferi* antigens determined in the method are antibodies to *B. burgdorferi* Osp A, Osp C, and Osp F.

The method is suitable for determining the presence or the absence of the antibodies using any suitable system or device. In various embodiments, the antibodies are determined using a lateral flow device or a fluorescent bead-based multiplex assay.

The invention included determining a test level of antibodies to *B. burgdorferi* Osp A, Osp C, and Osp F, and based upon a comparison of the test level of the Osp A, Osp C, and Osp F antibodies to the reference, identifying the mammal as vaccinated against *B. burgdorferi* and/or as having an early, intermediate or chronic *B. burgdorferi* infection. In one embodiment, the reference is a range of values for median fluorescence intensities.

In a specific aspect of the invention, the method comprises:
  i) identifying the mammal as vaccinated against but not infected by *B. burgdorferi* based on determining antibodies to OspA and an absence of antibodies to OspC or OspF;
  ii) identifying the mammal as having an early *B. burgdorferi* infection based on determining antibodies to OspC and an absence of antibodies to OspA and OspF;
  iii) identifying the mammal as having chronic *B. burgdorferi* infection based on determining antibodies to OspF and an absence of antibodies to OspA and OspC;
  iv) identifying the mammal as vaccinated against and having an early *B. burgdorferi* infection based on determining antibodies to OspA and OspC and an absence of antibodies to OspF;
  v) identifying the mammal as vaccinated against and having a chronic *B. burgdorferi* infection based on determining antibodies to OspA and OspF and an absence of antibodies to OspC;
  vi) identifying the mammal as having an intermediate *B. burgdorferi* infection based on determining antibodies to OspC and OspF and an absence of antibodies to OspA; or
  vii) identifying the mammal as having been vaccinated against and having an intermediate *B. burgdorferi* infection based on determining the presence of antibodies to OspC, OspF and OspA.

Compositions and kits comprising novel isolated protein comprising *B. burgdorferi* proteins and isolated nucleic acids encoding them are also included.

DETAILED DESCRIPTION OF THE INVENTION

Figure 1:
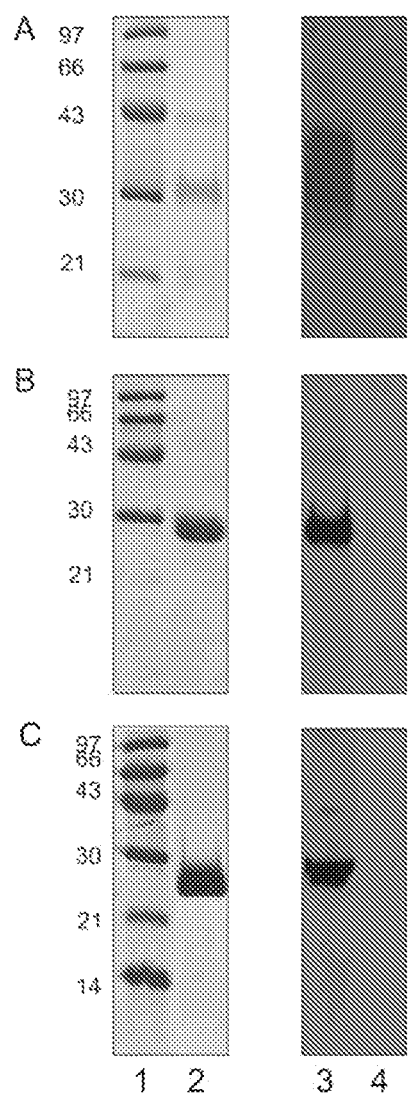
FIG. 1: Purified recombinant *B. burgdorferi* OspA (A), OspC (B) and OspF (C) proteins and their detection using sera from vaccinated or infected dogs by immunoblotting. Left panels: The recombinant proteins were separated by 15% SDS-PAGE under reducing conditions and stained with Coomassie Brilliant Blue (1=molecular weight marker; 2=purified recombinant *B. burgdorferi* protein). Right panels: The proteins were then transferred to polyvinylidene fluoride (PVDF) membranes by WB and were incubated with canine sera that were pretested in a conventional, whole *B. burgdorferi* cell lysate WB (3=positive serum; 4=negative serum).

The present invention provides a method for diagnosing Lyme disease status in a mammal. In general, the method comprises, in a biological sample obtained or derived from a mammal, determining antibodies to *Borrelia burgdorferi* (*B. burgdorferi*) outer surface proteins (Osp) OspA, OspC, and OspF. Based upon determining the OspA, OspC, and OspF antibodies, the mammal can be diagnosed as infected or not infected with *B. burgdorferi*. In various embodiments, the method provides for identifying a mammal as having been vaccinated against *B. burgdorferi* and/or as having an early, intermediate or chronic *B. burgdorferi* infection. The invention also provides compositions comprising novel isolated *B. burgdorferi* proteins and fragments thereof.

Lyme disease "status" as used herein refers to a mammal's antibody profile in respect of antibodies that specifically recognize *B. burgdorferi* OspA, OspC, and OspF. Determining Lyme disease status can include a determination that the mammal falls into one of the following categories: i) vaccinated against but not infected by *B. burgdorferi*; ii) having an early *B. burgdorferi* infection; iii) having chronic *B. burgdorferi* infection; iv) vaccinated against and having an early *B. burgdorferi* infection; v) vaccinated against and having a chronic *B. burgdorferi* infection; vi) having an intermediate *B. burgdorferi* infection; vii) having been vaccinated against and having an intermediate *B. burgdorferi* infection; or viii) not having been vaccinated against *B. burgdorferi* and not having a *B. burgdorferi* infection. As used herein, "early" infection means an infection that is 2 to 6 weeks old. A "chronic" or "late" infection means an infection that is 5 months or longer. An intermediate infection is an infection that is from 6 weeks to 5 months old.

The method of the invention is useful for determining Lyme disease status in any mammal. In particular embodiments, the mammal is a human, an equine, a canine or a human. Equines include members of the taxonomical family Equidae. In certain embodiments, the equine diagnosed according to the invention is a horse. Canines include members of the taxonomical family Canidae. In certain embodiments, the canine diagnosed according to the invention is a dog, such as a domesticated dog.

The biological sample tested in the method can be any biological sample that would be expected to contain antibodies. The biological sample is preferably a biological liquid. In various embodiments, the biological sample comprises blood, serum, or cerebral spinal fluid (CSF). The biological sample can be obtained from the mammal using any suitable technique and can be used directly in determining the presence or absence of the antibodies. Alternatively, the sample can be derived from the biological sample by subjecting it to a processing step, such as a processing step performed to isolate or purify blood, serum, CSF, or components of any such biological liquids.

In general, Lyme disease status can be ascertained according to the invention using the matrix set forth in Table 1, where "+" means a presence of antibodies that specifically recognize the indicated Osp antigen and "−" means an absence of such antibodies.

TABLE 1

| Osp A | Osp C | Osp F | Lyme Disease Status |
|-------|-------|-------|---------------------|
| + | − | − | Vaccinated |
| − | + | − | Infection - Early (2-3 weeks) |
| − | − | + | Infection - Chronic |
| + | + | − | Infection - Early & Vaccinated |
| + | − | + | Infection - Chronic & Vaccinated |
| − | + | + | Infection - Intermediate |
| + | + | + | Infection - Intermediate & Vaccinated |
| − | − | − | Infection - None & Not Vaccinated |

The matrix set forth in Table 1 was generated from testing and validating numerous biological samples obtained from a multitude of horses and dogs as will be more fully appreciated from the description and Examples below.

Table 1 illustrates a summary of data that highlight several non-limiting useful aspects of the invention. For example, it is clear from Table 1 that the presence or absence of antibodies to each of OspA, OspC and OspF is important to provide a definitive assessment of Lyme disease status. It particular it is clear that determining antibodies to OspA alone can provide a false positive for *B. burgdorferiv* infection, and can also provide a false negative result for early and chronic infections. Likewise, determining only an absence of antibodies to OspA and an absence of antibodies to OspC can yield a false negative result for chronic infection. Further, a definitive diagnoses of not having been infected and not having been vaccinated can be made by determining an absence of antibodies to each of OspA, OspC, and OspF, without having to determine any other antibody or indicator of *B. burgdorferi* infection. Thus, the recognition that determining the status of antibodies directed to all three OspA, OspC, and OspF antigens is an important feature of the invention and provides an unexpected benefit over previously available tests. In this regard, the invention can be practiced by determining antibodies to OspA, OspC, and OspF only, and therefore not determining antibodies to any other *B. burgdorferi* antigen. In one embodiment of the invention, antibodies to a BBK32 protein are not determined. BBK32 protein is described in U.S. patent publication no. 20060034862, from which the description of BBK32 proteins and the description of antibodies directed to such proteins is incorporated herein by reference.

In one embodiment, the method provides for diagnosis of Lyme disease status in a mammal by determining the presence or absence of antibodies specific for Osp A, Osp C, and Osp F, comprising: i) identifying the mammal as vaccinated against but not infected by *B. burgdorferi* based on determining antibodies to OspA and an absence of antibodies to OspC or OspF; ii) identifying the mammal as having an early *B. burgdorferi* infection based on determining antibodies to OspC and an absence of antibodies to OspA and OspF; iii) identifying the mammal as having chronic *B. burgdorferi* infection based on determining antibodies to OspF and an absence of antibodies to OspA and OspC; iv) identifying the mammal as vaccinated against and having an early *B. burgdorferi* infection based on determining antibodies to OspA and OspC and an absence of antibodies to OspF; v) identifying the mammal as vaccinated against and having a chronic *B. burgdorferi* infection based on determining antibodies to OspA and OspF and an absence of antibodies to OspC; vi) identifying the mammal as having an intermediate *B. burgdorferi* infection based on determining antibodies to OspC and OspF and an absence of antibodies to OspA; vii) identifying the mammal as having been vaccinated against and having an intermediate *B. burgdorferi* infection based on determining the presence of antibodies to OspC, OspF and OspA; or viii) identifying the mammal as not having been vaccinated against *B. burgdorferi* and not having a *B. burgdorferi* infection based on an absence of antibodies to OspC, OspF and OspA.

In various aspects of the invention, the OspA, OspC, and OspF antibodies can be considered test antibodies. In order to determine Lyme diseases status, the levels of test antibodies determined from a biological sample obtained or derived from a mammal can be compared to a reference.

In one embodiment, the invention provides a method for diagnosing Lyme disease status in a mammal comprising, in a biological sample obtained or derived from the mammal, determining a test level of antibodies to *B. burgdorferi* OspA, OspC, and OspF, and based upon a comparison of the test level of the OspA, OspC, and OspF antibodies to a reference, identifying the mammal as vaccinated against *B. burgdorferi* and/or as having an early, intermediate or chronic *B. burgdorferi* infection.

In one embodiment, the reference is used to determine the presence or absence of antibodies in the test sample. A reference can also be used for obtaining an estimate of the level of test antibodies. The reference can be established in parallel with the test sample, can be pre-established or established at a later time.

Generally, reference values are obtained by using different but known quantities of the variable of interest (i.e., antibodies and/or antigens, as the case may be) and can be obtained by methods known to those of ordinary skill in the art. The reference can be a single value or a range of values. For example, a reference can be a standardized curve or an area on a graph. In a particular embodiment, a reference can be obtained using a known antigen to which antibodies in the sample would be expected to recognize. The antigen is preferably the antigen which will be used for determining antibodies in a test sample. By exposing one or more levels of the antigen to one or more levels of antibodies expected to be in the sample, a reference single value, a range of values, a graph, etc. can be established.

In one embodiment, the reference can comprise a positive control. In one embodiment, the positive control is located on or in the same platform as used for the test sample. For example, the positive control can be present on a lateral flow device on which one or more distinct antigens at distinct locations and/or levels are also placed. This configuration provides for a signal from the control reference under test conditions irrespective of whether test antibodies are present or absent in the sample that is analyzed, and can provide a confirmation that the test is working properly. The positive control can, for example, produce a signal that is perceptible by a human or machine.

In various aspects of the invention, the test antibodies can be compared to a reference to provide a qualitative or quantitative determination of the level of test antibodies to the *B. burgdorferi* antigens. In either case, by comparison to the reference, the level of test antibodies can be characterized as having been present in, or absent from, the sample that is analyzed in the method of the invention.

A reference can also be configured such that it will not generate a signal or such that any signal generated from it will be regarded as background signal. Typically, this is referred to as a negative control and contains all reaction components except the specific antigen to which the test antibodies are expected to bind. Alternatively, the negative control can also contain a non-specific protein or antigen—such as bovine serum albumin or the like.

In certain embodiments, the level of test antibodies is compared to a reference that comprises one or more ranges of values. In certain non-limiting embodiments, a level of test antibodies that falls into a first reference value range signifies a high level of test antibodies that is informative as to the Lyme disease status of the mammal. A level of test antibodies that falls into a second reference value range signifies a low level (which can include an undetectable level or a complete absence) of the test antibodies which is also informative as to the Lyme disease status of the mammal. A level of test antibodies that falls into a third reference value range can signify a need for additional testing to be performed.

References comprised of a range of values can be generated by, for example, determining an average level of antibodies from groups of mammals with confirmed early, chronic or intermediate *B. burgdorferi* infection, or confirmed to not have *B. burgdorferi* infection, and/or confirmed to have not been vaccinated against *B. burgdorferi* infection.

Any suitable technique, device, system and/or reagents can be used to detect the OspA, OspC, and OspF *B. burgdorferi* antibodies, and/or combinations thereof. In general, the method of detecting the antibodies involves using OspA, OspC, and OspF proteins or fragments thereof in physical association with a solid matrix. The fragments of the proteins are those which would be expected to be recognized by antibodies produced in a mammal by vaccination against or infection with *B. burgdorferi*. The amino acid composition of such fragments can be identified using ordinary skill in the art. The proteins and/or the fragments may be obtained, isolated or derived from *B. burgdorferi*, or they may be produced recombinantly using any of a wide variety of conventional methods. The solid matrix to which the OspA, OspC, and OspF *B. burgdorferi* proteins or fragments thereof are in physical association can be any suitable solid matrix. The solid matrix can be present in and/or be a part of a multi-well assay plate, beads, such as fluorescently labeled beads, microspheres, a filter material, a lateral flow device or strip, or any other form or format that is suitable for keeping the proteins in a position whereby antibodies present in or otherwise derived from a biological sample obtained from a mammal can be captured and be detected. The proteins may be covalently or non-covalently associated with the solid matrix.

In one embodiment, the OspA protein comprises the sequence of SEQ ID NO:1: MKKYLLGIGLILALIACKQNVSSLDEKNSVSVDLPGEMKV-LVSKEKNKDGKYDLIAT VDKLELKGTSDKNNGSGV-LEGVKADKSKVKLTISDDLGQTTLEVFKEDGKTLV-SKK VTSKDKSSTEEKFNEKGEVSEKII-TRADGTRLEYTGIKSDGSGKAKEVLKGYVLEGTL TAEKTTLVVKEGTVTLSKNISKSGEV-LVELNDTDSSAATKKTAAWNSGTSTLTITVN SKKT-KDLVFTKENTITVQQYDSNGTKLEG-SAVEITKLDEIKNALK, or a fragment thereof.

In one embodiment, the OspC protein comprises the sequence of SEQ ID NO:2: MKKNTLSAILMTLFLFIS-CNNSGKDGNTSANSADESVKGPN-LTEISKKITDSNAVLLA VKEVEALLSSIDELAKAIGK-KIKNDGSLDNEANRNESLLAGAYTISTLITQKLSKL-NGS EGLKEKIAAAKKCSEEFSTKLKDN-HAQLGIQGVTDENAKKAILKANAAGKDKGVEE LEKLSGSLESLSKAAKEMLANS-VKELTSPVVAESPKKP, or a fragment thereof.

In one embodiment, the OspF comprises the sequence of SEQ ID NO:3: MNKKMFIICAVFALIISCKN-YATSKDLEGAVQDLESSEQNVKKTE-QEIKKQVEGFLEI LETKDLNKLDTKEIEKRIQELKEK-IEKLDSKKTSIETYSEYEEKLKQIKEKLKGKADLE DKLKGLEDSLKKKKEERKKALEDAKKK-FEEFKGQVGSATGVTTGHRAGNQGSIGA QAWQ-CANSLGLGVSYSSSTGTDSNELANKVID-DSIKKIDEELKNTIENNGEVKKE, or a fragment thereof.

The amino acid sequences of the Osp proteins used in the assays described in the Examples presented herein are novel. In particular, Table 2A sets forth differences from previously published *B. burgdorferi* Genbank sequences.

TABLE 2A

Degree of homology with previously existing *B. burgdorferi* Genbank sequences

|  | OspA | OspC | OspF |
|---|---|---|---|
| Plasmid whole sequence | OspA/pRSET-1 | OspC/pCR4-2 | OspF/pCR4-5 |
| Size (bp/aa) | 822bp/273aa | 636bp/211aa | 684bp/227aa |
| Genbank accession no. | HM756743 | HM756744 | HM756745 |
| Previously available accession no. from B31 | NC_001857 | NC_001903 | L13925 |
| Size B31 gene (bp/aa) | identical | 633bp/210aa | 693bp/231aa |
| Nucleotide homology (%) | 99.8% | 85.8% | 91.6% |
| Amino acid homology (%) | 99.3% | 79.8% | 85.3% | bp = base pair;
aa amino acid

TABLE 2B

Sequences used for expression and rOspA, rOspC and rOspF used in multiplex assays.

|  | OspA | OspC | OspF |
|---|---|---|---|
| Bases used for expression based on whole gene seq. | 1-666 of SEQ ID NO: 14 | 52-636 of SEQ ID NO: 16 | 178-684 of SEQ ID NO: 18 |
| Forward primer | OspAFBam | OspCF-Bam2 | OspF-178-B |
| Reverse primer | OspARKpn | OspCR-Kpn | OspF-684-K |
| Size (bp/aa) | 666bp/222aa | 585bp/194aa | 507bp/168aa |
| Plasmid used for expression | OspA(1A)/pQE30-2 | OspC2(B/K)/pQE30-2 | OspF(3A)/pQE30-1 |

TABLE 2C

Primers for expression cloning.

|  | forward | reverse |
|---|---|---|
| OspA (1-666) | Cgcggatccatgaaaaaatatttattggg (SEQ ID NO: 4) | Ggcggtacctcaagttgaagtgcctgaattcc (SEQ ID NO: 5) |
| OspC (52-636) | Cgcggatcctcttgtaataattcagggaaag (SEQ ID NO: 6) | Ggcggtacctcaaggttttttggactttctgc (SEQ ID NO: 7) |
| OspF (178-684) | Cgcggatccgagacgaaagatttgaataa (SEQ ID NO: 8) | Ggcggtaccttattcttttttgacttctcc (SEQ ID NO: 9) |

Restriction sites are underlined; stop codons are in bold.

The nucleotide and amino acid sequences associated with Genbank accession no. HM756743, HM756744 and HM756745 were determined in the performance of this invention and did not first become publicly accessible until at the earliest Jan. 1, 2011. Thus, in various embodiments and as set forth in Table 2B, the Osp antigens used in the method of the invention to capture antibodies directed to them comprises the amino acid sequence encoded by nucleotides 1-666 of the OspA nucleotide sequence described herein (SEQ ID NO:15), and/or the amino acid sequence encoded by nucleotides 52-636 of the OspC nucleotide sequence (SEQ ID NO:17), and/or the amino acid sequence encoded by nucleotides 178-684 of the OspF nucleotide sequence disclosed herein (SEQ ID NO:19).

In various embodiments, the invention provides compositions comprising isolated or recombinant proteins which comprise or consist of the sequences of SEQ ID NO:1, SEQ ID NO:2 or SEQ ID NO:3. Fragments of these proteins are also provided and include but are not limited to fragments comprising or consisting. The proteins or fragments thereof can be provided as components of compositions and/or the kits that are described further herein. For example, they can be provided as part of any system, device or composition that can be used for determining the presence or absence of *B. burgdorferi* antibodies that can specifically recognize them. In one embodiment, the proteins can be provided in physical association with a solid matrix. In one embodiment, the solid matrix is a bead (microsphere).

In non-limiting examples, the antibodies to *B. burgdorferi* can be detected and discriminated from one another using any immunodetection techniques, which include but are not necessarily limited to Western blot, enzyme-linked immunosorbent assay (ELISA), a snap test, multiplex antibody detection techniques of various kinds, or any modification of such assays that are suitable for detecting antibodies of interest.

In one embodiment, OspA, OspC and OspF antigens are provided in separate locations in physical association with a solid matrix configured on or as a lateral flow strip. A biological sample obtained or derived from a mammal can be analyzed using the strip such that the presence of distinct antibodies that specifically recognize the OspA, OspC and OspF antigens will produce separate signals which indicate the presence or absence of antibodies to each antigen. The absence of antibodies to all of the antigens is indicative that the mammal has not been vaccinated and has not been infected with *B. burgdorferi*. The presence and absence of antibodies can be interpreted generally in connection with the matrix set forth in Table 1.

In one embodiment, antibodies to OspA, OspC and OspF, or combinations thereof, are detected using OspA, OspC and OspF antigens coupled to fluorescent beads. The fluorescent beads can be any suitable fluorescent beads, examples of which are commercially available from, for example, Luminex Corporation. The beads can each be labeled with different or the same fluorescently detectable moieties. The beads can be coded such that beads coupled to each of the distinct antigens can be discriminated from one another. Antibodies present in a biological sample obtained or derived from a mammal will bind to the antigen-coupled fluorescent beads according to the antigens with which each bead type is coupled. An anti-species specific antibody conjugated to a detectable label can be used to detect the presence or absence of antibodies to OspA, OspC and OspF, or combinations thereof, which can then be used to diagnose Lyme disease status according to, for example, the matrix set forth in Table 1.

Figure 9:
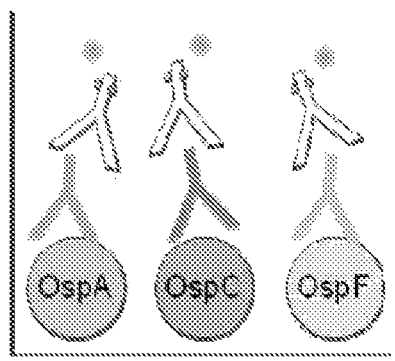
FIG. 9: Illustration of a one embodiment of a multiplex assay for detection of antibodies to *B. burgdorferi*. (1) Recombinant *B. burgdorferi* OspA, OspC and OspF antigens are coupled to fluorescent beads. (2) Samples (e.g. serum, CSF or other body fluids) are incubated with all three fluorescent beads simultaneously. (3) A biotinylated anti-species specific immunoglobulin antibody is added to the assay. (4) Streptavidin-phycoerythrin is added as a reporter dye. The assay is then measured in a multiplex analyzer that detects the fluorescent bead code and the reporter dye for each individual bead assay.

One illustrative example of a multiplex fluorescent bead-based assay for determining the antibodies according to the invention is depicted in FIG. 9. As can be seen from FIG. 9, (1) recombinant *B. burgdorferi* OspA, OspC and OspF antigens are coupled to fluorescent beads; (2) Samples (e.g. serum, CSF or other body fluids) are incubated with all three fluorescent beads simultaneously; (3) A biotinylated anti-species specific immunoglobulin antibody is added to the assay; (4) Streptavidin-phycoerythrin is added as a reporter dye. The assay is then measured in a multiplex analyzer that detects the fluorescent bead code and the reporter dye for each individual bead assay. Moieties such as streptavidin and biotin and their derivatives and other reporter dyes can be substituted with any of a variety of commercially available substitute agents that can perform the same or similar functions in the multiplex assay.

Output data from fluorescence-based antibody detection methods can be represented in various ways well known to those skilled in the art. In one embodiment, fluorescence-based antibody detection can be presented as a median fluorescent intensity (MFI). In the present invention, we have determined that certain MFI value ranges can be used for determining Lyme disease status, particularly for equines and canines. MFI values suitable for use in the invention include those set forth in Table 3.

TABLE 3

Negative, equivocal and positive interpretation ranges for canine or equine samples using a fluorescent bead-based multiplex assay for antibodies to *B. burgdorferi* OspA, OspC and OspF.

| B. burgdorferi | | Multiplex assay range (MFI) | |
| --- | --- | --- | --- |
| Antigen | Interpretation | canine | equine |
| OspA | Negative | <500 | <1000 |
|  | Equivocal | ≥500 <1,500 | ≥1000-2000 |
|  | Positive | ≥1,500 | >2000 |
| OspC | Negative | <250 | <500 |
|  | Equivocal | ≥250 <1,000 | ≥500-1000 |
|  | Positive | ≥1,000 | >1000 |
| OspF | Negative | <750 | <750 |
|  | Equivocal | ≥750 <1,500 | ≥750-1250 |
|  | Positive | ≥1,500 | >1250 |

Equivocal results set forth in Table 3 are indicative that additional testing should be performed so that the sample can be classified as negative or positive.

In one embodiment, the method is performed to determine the Lyme disease status of an equine. This embodiment comprises, in a biological sample obtained from or derived from the equine, determining the presence or absence of OspA, OspC, and OspF antibodies. The presence or absence of the antibodies is determined using any suitable technique, which in one embodiment is a multiplex assay comprising the OspA, OspC, and OspF antigens provided in physical association with fluorescent beads. The OspA, OspC, and OspF antigens are contacted with a biological sample obtained or derived from an equine. Antibodies to the antigens, if present, will bind to the antigen and will thereby be immobilized on the antigen/fluorescent bead complexes. A detectably labeled anti-equine specific antibody is added and a multiplex analyzer is used to detect the fluorescent beads and the detectable label from the anti-equine specific antibody to generate an MFI value for each of the OspA, OspC, and OspF antibodies. The presence or absence of the antibodies is determined in accordance with the equine values set forth in Table 3 and a determination of Lyme disease status is made according to the matrix set forth in Table 1. The same rationale applies to analysis of a biological sample obtained or derived from a canine, whereby the MFI values set forth in Table 3 for canine samples are used to determine the presence or absence of the antibodies, but an anti-canine specific antibody is used instead of an anti-equine specific antibody. Thus, based upon determining MFI values for the OspA, OspC, and OspF antibodies, the equine or canine can be diagnosed as infected or not infected with B. burgdorferi and moreover can be identified as having been vaccinated against B. burgdorferi and/or as having an early, intermediate or chronic B. burgdorferi infection.

In various embodiments, the invention further comprises fixing the determination of the antibodies in a tangible medium. The tangible medium can be any type of tangible medium, such as any type of digital medium, including but not limited a DVD, a CD-ROM, a portable flash memory device, etc. The invention includes providing the tangible medium to an animal owner, a breeder, and/or an animal health care provider to develop a recommendation for treatment of a mammal that has been determined to have a Lyme disease infection.

Also provided in the present invention is a device for determining the antibodies. In one embodiment, the device is a lateral flow device which comprises OspA, OspC and OspF antigens in physical association with a solid matrix. In one embodiment, the OspA, OspC and OspF are the only B. burgdorferi antigens provided in association with the solid matrix. In one embodiment, the OspA, OspC and OspF antigens provided with the device comprise or consist of amino acid sequences disclosed herein.

Also provided are kits for detecting the presence or absence of the antibodies. In one embodiment, the kits comprise OspA, OspC and OspF antigens in physical association with a solid matrix. In one embodiment, the OspA, OspC and OspF are the only B. burgdorferi antigens provided with the kit. The kit can include fluorescent beads as the solid matrix. The kit can further include the antigens and or the beads in one or more separate vials. The kit may optionally include instructions for use of the kit.

The following Examples are intended to illustrate but not limit the present invention.

EXAMPLE 1

This Example provides a description of one embodiment of the method demonstrating its enhanced utility for determining Lyme disease status in canines. In particular, in this Example, we describe the development and validation of a fluorescent bead-based multiplex assay for simultaneous detection of antibodies specific for B. burgdorferi OspA, OspC and OspF antigens in canine serum. The validation was performed by comparing multiplex assay results to the recommended confirmatory test for diagnosing Lyme disease which is Western blotting (WB) (see, for example, www.cdc.gov/ncidod/dvbid/lyme/ld_humandisease_diagnosis.htm). Among other advantages of the present invention, and contrary to previous studies in canines which taught that OspC was not a suitable diagnostic marker, the current invention clearly demonstrates otherwise. In particular, test results presented in this Example provide for enhanced determination of Lyme disease status in canines as compared to any currently available Lyme disease testing methods, and afford better definition of a canine's current vaccination and infection status by determining antibodies to OspA, OspC and OspF.

The following materials and methods were used to obtain the results presented in this Example.

Cloning of *Borrelia burgdorferi* Genes

B. burgdorferi OspA, OspC and OspF proteins were expressed in *E. coli* and were used as antigens in the multiplex assay. DNA was isolated from B. burgdorferi originating from infected *Ixodes dammini* ticks collected in a forested area in Westchester County, New York (Appel et al. 1993). The complete OspC and OspF genes were amplified by PCR using Pfu DNA polymerase (Stratagene, La Jolla, Calif., USA). OspC and OspF primers were designed from Genbank accessions NC_001903 and L13925, respectively. Positions of the primers used for amplification are given in parentheses: OspC forward (1-23) 5' atgaaaaagaatacattaagtgc 3' SEQ ID NO:10; OspC reverse (633-607) 5' ttaaggtttttttggactttctgccac 3' SEQ ID NO:11; OspF forward (16-44) 5' atgaataaaaaaat-gtttattatttgtgc 3' SEQ ID NO:12; and OspF reverse (708-688) 5' ttattctttttgacttctcc 3' SEQ ID NO:13. The PCR was performed as previously described (Wagner et al., 2001). The PCR products were cloned into pCR4 TopoBlunt vector (Invitrogen, Carlsbad, Calif., USA) and sequenced using an ABI automatic sequencer at the BioResource Center, Cornell University. The OspA gene was amplified from the plasmid OspA/pRSET. The nucleotide sequences of the complete coding regions of the cloned genes were submitted to Genbank and received the accession numbers HM756743 (OspA), HM756744 (OspC) and HM756745 (OspF).

Expression and Purification of B. burgdorferi Genes

Expression cloning was performed based on the following DNA sequences which are also referred to in Table 2.

OspA (822 bp), Genbank accession HM756743

SEQ ID NO: 14 atgaaaaaatatttattgggaataggtctaatattagccttaatagcatgtaagcaaatgttagcagccttgacgagaaaaacagcgtttc agtagatttgcctggtgaaatgaaagttcttgtaagcaaagaaaaaaacaaagacggcaagtacgatctaattgcaacagtagacaag cttgagcttaaaggaacttctgataaaaacaatggatctggagtacttgaaggcgtaaaagctgacaaaagtaaagtaaaattaacaattt ctgacgatctaggtcaaaccacacttgaagttttcaaagaagatggcaaaacactagtatcaaaaaaagtaacttccaaagacaagtcat caacagaagaaaattcaatgaaaaaggtgaagtatctgaaaaaataataacaagagcagacggaaccagacttgaatacacaggaa ttaaaagcgatggatctggaaaagctaaagaggttttaaaaggctatgttcttgaaggaactctaactgctgaaaaaacaacattggtgg ttaaagaaggaactgttactttaagcaaaaatattttcaaaatctggggaagttttagttgaacttaatgacactgacagtagtgctgctacta aaaaaactgcagcttggaattcgggcacttcaactttaacaattactgtaaacagtaaaaaaactaaagaccttgtgtttacaaaagaaaa cacaattacagtacaacaatacgactcaaatggcaccaaattagaggggtcagcagttgaaattacaaaacttgatgaaattaaaaacg ctttaaaataa

SEQ ID NO: 15

MKKYLLGIGLILALIACKQNVSSLDEKNSVSVDLPGE

MKVLVSKEKNKDGKYDLIATVDKLELKGTSDKNNGS

GVLEGVKADKSKVKLTISDDLGQTTLEVFKEDGKTL

VSKKVTSKDKSSTEEKFNEKGEVSEKIITRADGTRLE

YTGIKSDGSGKAKEVLKGYVLEGTLTAEKTTLVVKE

GTVTLSKNISKSGEVLVELNDTDSSAATKKTAAWNS

GTST

OspC (636 bp), Genbank accession HM756744

SEQ ID NO: 16 atgaaaaagaatacattaagtgcaatattaatgactttattttatttatatcttgtaataattcagggaaagatgggaatacatctgcaaattct gctgatgagtctgttaaagggcctaatcttacagaaataagtaaaaaaattacggattctaatgcggttttacttgctgtgaaagaggttga agcgttgctgtcatctatagatgagcttgctaaagctattggtaaaaaaataaaaaacgatggtagtttagataatgaagcaaatcgcaac gagtcattgttagcaggagcttatacaatatcaaccttaataacacaaaaattaagtaaattaaacggatcagaaggtttaaaggaaaag attgccgcagctaagaaatgctctgaagagtttagtactaaactaaaagataatcatgcacagcttggtatacagggcgttactgatgaa aatgcaaaaaaagctattttaaaagcaaatgcagcgggtaaagataagggcgttgaagaacttgaaaagttgtccggatcattagaaag cttatcaaaagcagctaaagagatgcttgctaattcagttaaagagcttacaagccctgttgtggcagaaagtccaaaaaaaccttaa

SEQ ID NO: 17

SCNNSGKDGNTSANSADESVKGPNLTEISKKITDSNA

VLLAVKEVEALLSSIDELAKAIGKKIKNDGSLDNEAN

RNESLLAGAYTISTLITQKLSKLNGSEGLKEKIAAAK

KCSEEFSTKLKDNHAQLGIQGVTDENAKKAILKANA

AGKDKGVEELEKLSGSLESLSKAAKEMLANSVKELT

SPVVAESPKKP

OspF (684 bp), Genbank accession HM756745

SEQ ID NO: 18 atgaataaaaaaatgtttattatttgtgctgtttttgcgttgataatttcttgcaagaattatgcaactagtaaagatttagaaggggcagtgca agatttagaaagttcagaacaaaatgtaaaaaaaacagaacaagagataaaaaaacaagttgaaggattttagaaattctagagacga aagatttgaataaattggatacaaaagagattgaaaaacgaattcaagaattaaaggaaaaaatagaaaaattagattctaaaaaaactt ctattgaaacatattctgagtatgaagaaaaactaaaacaaataaaagaaaaattgaaaggaaaggcagatcttgaagataaattaaag ggacttgaagatagcttaaaaaagaaaaaagaggaaagaaaaaaagctttagaagatgctaagaagaaatttgaagagtttaaaggac aagttggatccgcgactggagtaactaccggcatagagctggaaatcaaggtagtattggggcacaagcttggcagtgtgctaatag tttggggttgggtgtaagttattctagtagtactggtactgatagcaatgaattggcaaacaaagttatagatgattcaattaaaaagattga tgaagagcttaaaaatactatagaaataatggagaagtcaaaaaagaataa

SEQ ID NO: 19

ETKDLNKLDTKEIEKRIQELKEKIEKLDSKKTSIETYS

EYEEKLQIKEKLKGKADLEDLKGLEDSLKKKEE

RKKALEDAKKKFEEFKGQVGSATGVTTGHRAGNQGS

IGAQAWQCANSLGLGVSYSSSTGTDSNELANKVIDDS

IKKIDEELKNTIENNGEVKKE

For expression cloning the OspA (bases 1-666), OspC (bases 52-636) and OspF (bases 178-684 of the above described DNA sequences) were first amplified by PCR using primers with BamHI (5') and KpnI (3') restriction sites. The genes were cloned into the pQE-30 Xa expression vector (Qiagen Inc., Valencia, Calif.) and were expressed as His-tagged proteins in *E. coli* SG13009 cells (Qiagen Inc., Valencia, Calif.) after induction with 1 mM IPTG. The bacteria were lysed in buffer containing 100 mM sodium phosphate, 10 mM Tris and 8M urea, pH 8.0. The lysates were diluted 1:5 in 40 mM imidazole buffer and the His-tagged proteins were purified on HisTrapFF columns using an AKTA-FPLC instrument (both GE Healthcare, Piscataway, N.J.). Protein concentrations were determined by BCA assay (Pierce, Rockford, Ill.).

SDS-PAGE and Western Blotting

SDS-PAGE, Western blotting and immunoblotting (the latter two here referred to as WB) were performed as described (Wagner et al., 2005). In brief, 2-4 μg/lane of the recombinant *B. burgdorferi* proteins were separated in 15% mini-gels (BioRad Laboratories, Hercules, Calif., USA) under reducing conditions. Gels were either stained with Coomassie Brilliant Blue or proteins were transferred to a membrane (PVDF, BioRad Laboratories, Hercules, Calif., USA) for immunoblotting. After transfer, a blocking step was performed using 5% (w/v) non-fat dry milk in Tris buffer (0.1M Tris, pH 7.6 containing 0.05% (v/v) Tween 20). The membranes were then incubated with canine serum diluted 1:10 in Tris buffer with 5% non-fat dry milk. A secondary peroxidase conjugated rabbit anti-dog IgG(H+L) antibody (Jackson ImmunoResearch Lab., West Grove, Pa.) was used for detection. After incubation of each antibody, membranes were washed three times with Tris buffer and antibody binding was visualized by the ECL chemiluminescence method (Amersham Bioscience, Piscataway, N.J., USA). In addition, all sera used for validation of the multiplex assay were tested by conventional *B. burgdorferi* WB using whole bacterial lysate as previously described (Appel et al. 1993).

Coupling of Recombinant *B. Burgdorferi* Antigens to Fluorescent Beads

A total of 100 μg of each purified recombinant *B. burgdorferi* protein was coupled to fluorescent beads (Luminex Corp.). OspA was coupled to bead 33, OspC to bead 34, and OspF to bead 37. The coupling was performed according to the recommended protocol from the bead supplier Luminex Corporation. (See, www.luminexcorp.com/uploads/data/Protein%20Protocols%20FAQs/Protein%20Coupling%20Protocol%200407%2010207.pdf). In brief, the entire procedure was performed at room temperature. All centrifugation steps were performed at 14,000×g for 4 minutes. Afterwards, the beads were resuspended by vortexing and sonication for 20 seconds. For activation, $5\times10^6$ beads were washed once in $H_2O$. Beads were resuspended in 80 μl of 100 mM sodium phosphate buffer, pH 6.2. Then, 10 μl Sulfo-NHS (50 mg/ml,) and 10 μl 1-ethyl-3-[3-dimethylaminopropyl]carbodiimide hydrochloride (EDC, 50 mg/ml, both from Pierce Biotechnology Inc., Rockford, Ill.) were added and incubated for 20 minutes. The beads were washed twice with 50 mM 2-[N-morpholino]ethanesulfonic acid, pH 5.0 (MES) and resuspended in MES solution. These activated beads were used for coupling of the recombinant *B. burgdorferi* antigens. The coupling was performed for three hours with rotation. After coupling, the beads were resuspended in blocking buffer (PBS with 1% (w/v) BSA and 0.05% (w/v) sodium azide) and incubated for 30 minutes. The beads were washed three times in PBS with 0.1% (w/v) BSA, 0.02% (v/v) Tween 20 and 0.05% (w/v) sodium azide (PBS-T), counted and stored in the dark at 2-8° C.

Luminex Assay

Beads coupled with OspA, OspC and OspF were sonicated, mixed and diluted in blocking buffer to a final concentration of $1\times10^5$ beads/ml each. For the assay, $5\times10^3$ beads/each were used per microtiter well. All canine serum samples were diluted 1:600 in blocking buffer. Previously tested negative, low positive and high positive canine sera and beads incubated with blocking buffer alone were run as positive and negative controls on each assay plate. Millipore Multiscreen HTS plates (Millipore, Danvers, Mass.) were soaked with PBS-T using a ELx50 plate washer (Biotek Instruments Inc., Winooski, Vt.) for 2 minutes. The solution was aspirated from the plates and 50 μl of each control serum or sample was applied to the plates. Then, 50 μl of bead solution was added to each well and incubated for 30 minutes on a shaker at room temperature. The plate was washed with PBS-T and 50 μl of biotinylated rabbit anti-dog IgG(H+L) (Jackson Immunoresearch Laboratories, West Grove, Pa.) diluted 1:5000 in blocking buffer was added to each well and incubated for 30 minutes as above. After washing, 50 μl of streptavidin-phycoerythrin (Invitrogen, Carlsbad, Calif.) diluted 1:100 in blocking buffer was added. Plates were incubated for 30 minutes as above and washed. The beads were resuspended in 100 μl of blocking buffer and each plate was placed on the shaker for 15 minutes to resuspend the beads. The assay was analyzed in a Luminex IS 100 instrument (Luminex Corp.). The data were reported as median fluorescent intensities (MFI).

Serum Samples

All canine serum samples were submitted for serological testing of antibodies to *B. burgdorferi* to the Animal Health Diagnostic Center at Cornell University and were tested in a kinetic ELISA and by WB to detect antibodies to *B. burgdorferi*. Both assays used whole cell lysates of *B. burgdorferi* and were described previously (Appel et al. 1993, Jacobson et al. 1996). Two canine serum sample sets were used for this study:

First, 79 serum samples with available ELISA and WB results for antibodies to *B. burgdorferi* were used to establish the conditions of the bead-based assay for each antigen and for the comparison of results from singleplex and multiplex analysis. These 79 samples were selected to provide similar numbers of samples ranging from negative to high positive results by ELISA and WB and according to these results included sera from vaccinated and/or naturally infected dogs. Second, a total of 188 canine serum samples that were not tested previously were used for further multiplex assay validation. All samples were analyzed in parallel for antibodies to *B. burgdorferi* antigens by WB. The presence (positive) or absence (negative) of serum antibodies to the 31 kDa (OspA), 22 kDa (OspC) and 29 kDa (OspF) on the blots was determined blindly by an observer who was not aware of the multiplex assay results. The WB results provided a 'relative gold standard' for each antigen and were used for receiver operating curve (ROC) analysis and to determine interpretation ranges for antibodies to *B. burgdorferi* OspA, OspC and OspF antigens in the multiplex assay.

Statistical Analysis

For the comparison of results obtained by singleplex and multiplex assay formats the corresponding MFI values of all samples were compared for each *B. burgdorferi* antigen by calculating Spearman rank correlations. Mann-Whitney tests were performed to compare differences in multiplex assay MFI values for samples that were either negative or positive for the respective antigen when tested by WB. The Mann-Whitney tests were run with Gaussian approximation, 2-sided, with 95% confidence intervals and using $p<0.05$ as cut-off for significance. To determine the sensitivity and specificity for each bead assay within the multiplex assay format ROC curves were generated by using the WB result (positive/negative) of each serum sample and the corresponding protein as a 'relative gold standard' in comparison to the MFI value obtained for that sample and recombinant antigen using the multiplex assay. A likelihood ratio analysis was performed to define ranges of interpretation and diagnostic sensitivities and specificities in the multiplex assay. ROC curves and likelihood analyses were performed separately for each antigen. The Spearman rank correlations and the Mann-Whitney tests were performed using the GraphPad Prism program, version 5.01. The ROC curves were generated using the MedCalc program, version 11.2.0.0; 2010F. Schoonjans, Mariakerke, Belgium. The likelihood analysis was performed using Statistix 9.0, 2008, Analytical Software, Tallahassee, Fla., USA.

Results

Expression of *B. burgdorferi* Antigens

The extracellular parts of *B. burgdorferi* OspA, OspC and OspF proteins were expressed in *E. coli* (FIG. 1) and were 333, 194 and 169 amino acids in size, respectively. The resulting rOspA proteins had a calculated molecular weight of 30 kDa. In addition to the corresponding predominant protein at 30 kDa, two weaker proteins of 22 and 42 kDa were observed after purification suggesting minor contaminations with other proteins during affinity purification of rOspA. The calculated molecular weights were 17.5 kDa for rOspC and 15.2 kDa for rOspF. The resulting proteins found by SDS-PAGE were 29 kDa for rOspC and 27 kDa for rOspF suggesting dimerization of both proteins.

Development of a Fluorescent Bead-based Assay

Figure 2:
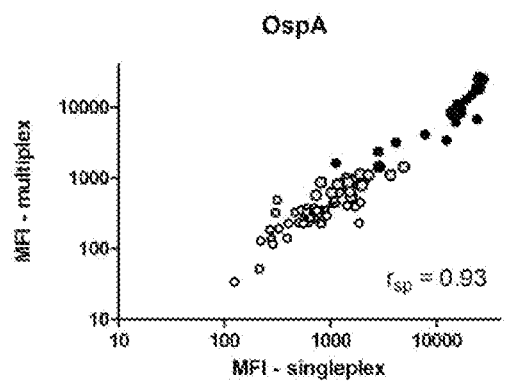
FIG. 2: Correlation of singleplex (single bead analysis) and multiplex assay results for the analysis of serum antibodies to *B. burgdorferi* OspA, OspC and OspF antigens. A total of 79 canine sera were used for the comparison. The data were color-coded according to the negative (white circles), equivocal (grey circles) and positive (black circles) interpretation ranges determined in Table 3. Spearman rank correlations were calculated for each of the antigens. MFI=median fluorescent intersity.
Figure 2:
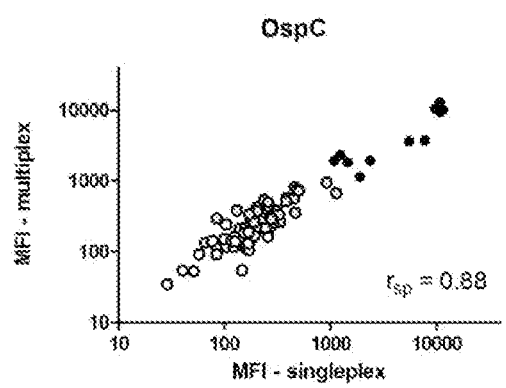
Figure 2:
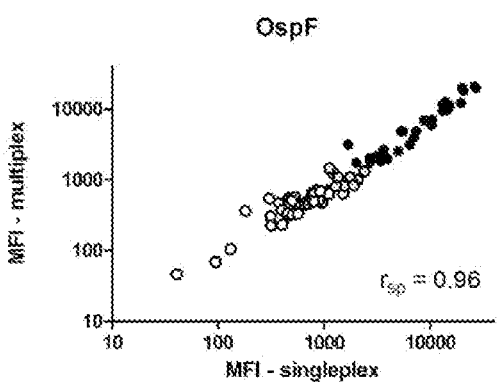

The recombinant *B. burgdorferi* OspA, OspC and OspF proteins were coupled to fluorescent beads. Pretested canine serum samples with known WB testing results for antibodies to *B. burgdorferi* were used to establish the conditions of each bead-based assay. Positive and negative controls were identified and included on each assay plate (Table 3). A total of 79 sera were then measured in singleplex assays with each individual antigen and in a multiplex assay using all three antigens simultaneously (FIG. 2). Spearman rank correlations between the singleplex and multiplex analyses were 0.93 (OspA), 0.88 (OspC) and 0.96 (OspF). The mean background values of the multiplex assay were determined by 40 runs without serum and were <10 MFI for the OspA and OspC assays and 80 MFI for OspF.

Table 4: MFI values (mean±standard deviations) for the OspA, OspC and OspF assays obtained by 20 separate multiplex assay runs using canine control serum samples (positive, low positive and negative) and background values (dilution buffer).

TABLE 4

|  | OspA | OspC | OspF |
|---|---|---|---|
| Positive serum | 10386 ± 2292 | 3759 ± 1012 | 21976 ± 2924 |
| Low positive serum | 965 ± 298 | 1125 ± 297 | 5336 ± 1289 |
| Negative serum | 201 ± 72 | 48 ± 17 | 244 ± 71 |
| Background (buffer) | 7 ± 2 | 4 ± 1 | 84 ± 4 |

Comparison of WB and Multiplex Assay Results for OspA, OspC and OspF

Figure 3:
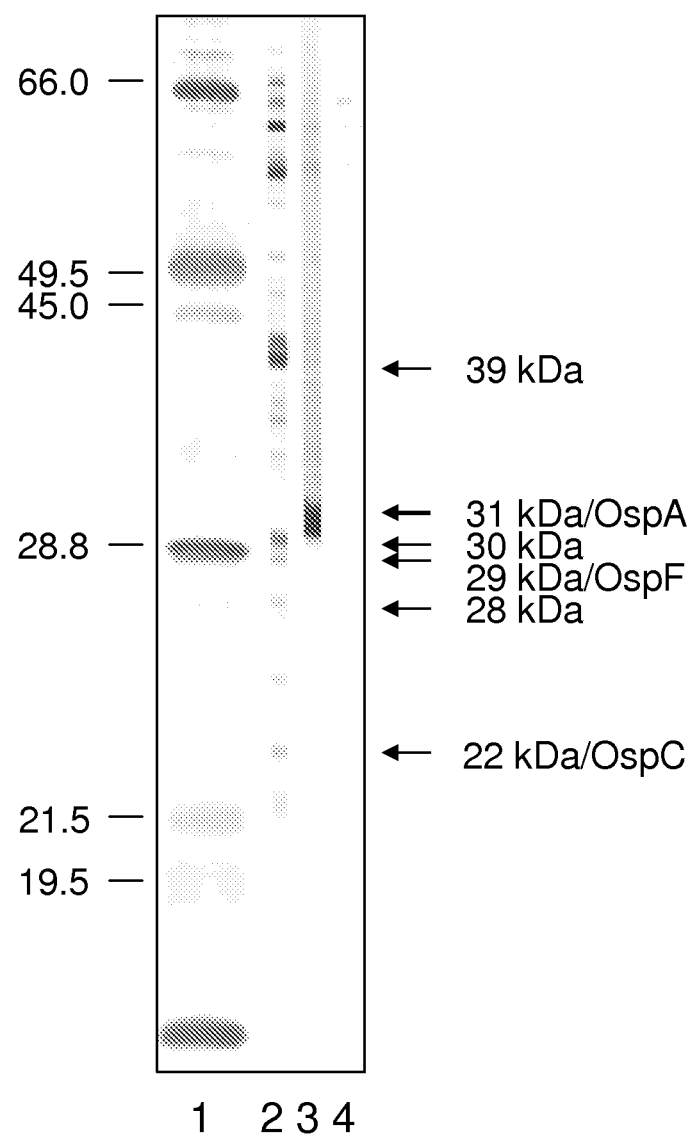
FIG. 3: Conventional WB for detection of antibodies to *B. burgdorferi* in canine serum. A whole *B. burgdorferi* cell lysate was separated on a 12% SDS gel under reducing conditions. The proteins were transferred by WB. The blot membrane was blocked with 5% milk and then incubated with different canine sera. A secondary peroxidase conjugated anti-canine immunoglobulin antibody was used for detection followed by a chromogenic substrate. Lane 1=molecular weight marker; lane 2=serum from an infected dog; lane 3=serum from a vaccinated dog; lane 4=negative canine serum. The slim arrows point to proteins indicative for infection of 22, 28, 29, 30 and 39 kDa, respectively. The bold arrow shows the 31 kDa protein confirming vaccination of the dog.
Figure 4:
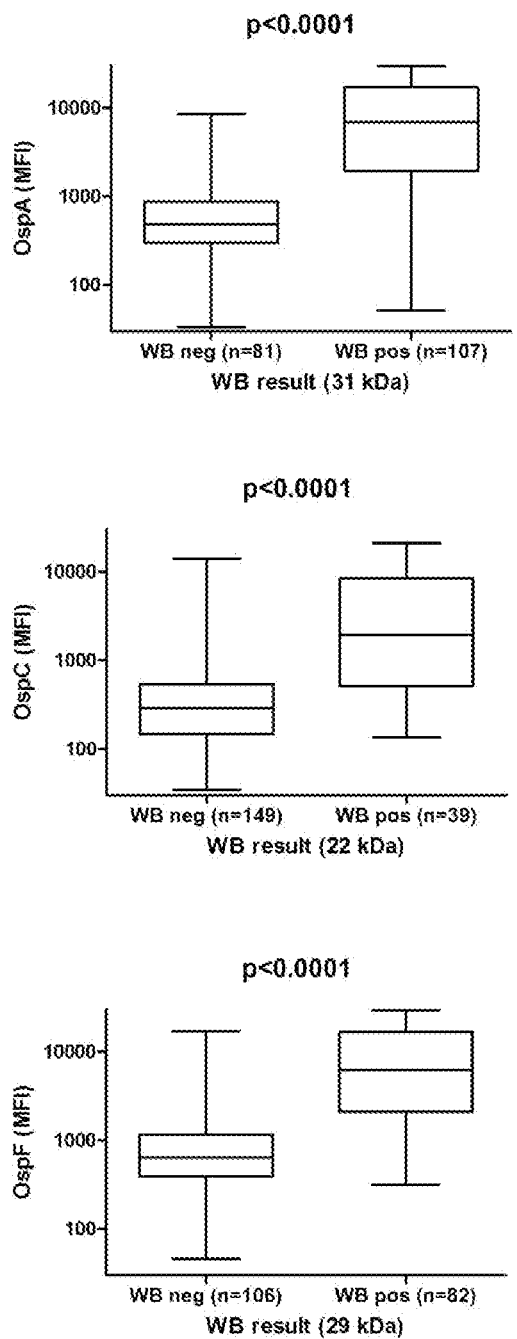
FIG. 4: Comparison of WB results (whole bacterial lysate) and multiplex analysis for *B. burgdorferi* OspA, OspC and OspF antigens. A total of 188 canine sera were tested by WB and were grouped as WB negative (neg) or WB positive (pos) for each antigen. The multiplex assay results for the WB neg and WB pos groups were compared using Mann-Whitney tests. MFI=median fluorescent intensity.
Figure 5:
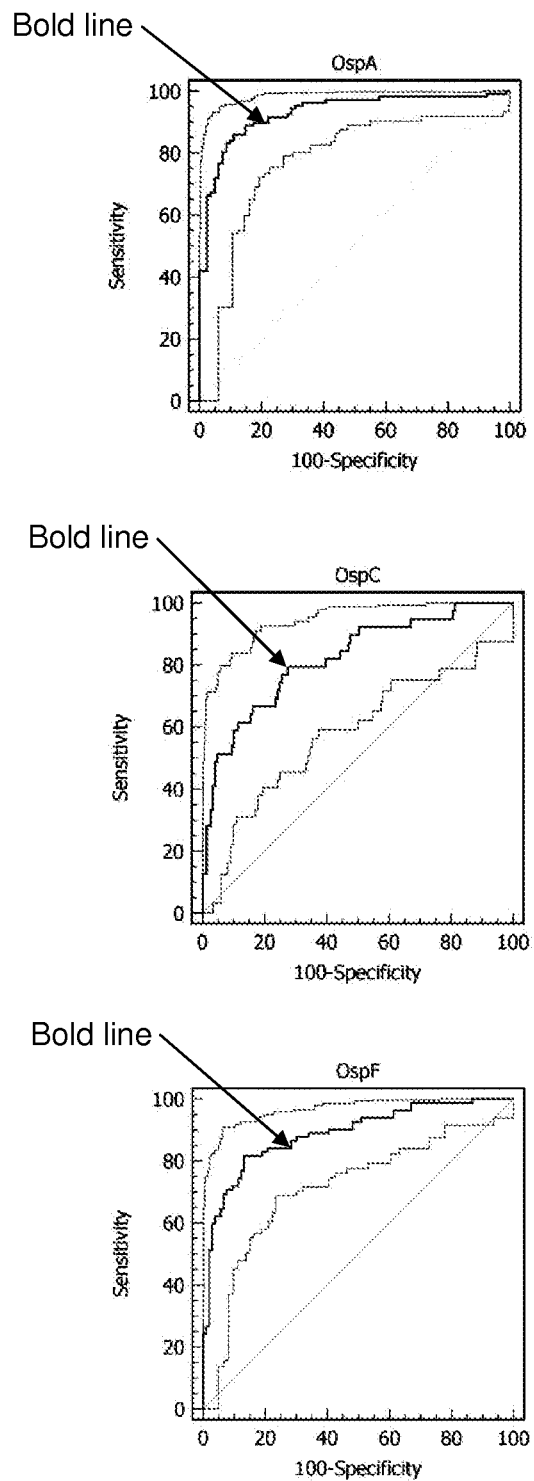
FIG. 5: Receiver operating curves (ROC) for detection of serum antibodies to *B. burgdorferi* OspA, OspC and OspF antigens by multiplex assay. The multiplex assay results were compared for each antigen to the presence or absence of serum antibodies to the corresponding *B. burgdorferi* protein detected by WB. Results from 188 canine serum samples were compared for each ROC curve. The areas under the curves (bold lines) are 0.93 for OspA, 0.82 for OspC and 0.89 for OspF. The dotted curves show the 95% confidence intervals. (Arrow shows bold line; 2 lines bracketing the bold line='dotted' lines.)

WB and multiplex assay results from 188 canine sera were compared for each protein. FIG. 3 shows the conventional WB results from an infected (lane 2), a vaccinated (lane 3), and a non-infected/non-vaccinated dog serum (lane 4). The OspA multiplex results were compared to the occurrence of the 31 kDa protein on the WB, OspC was compared to the 22 kDa protein, and OspF to the 29 kDa protein. The WB results were separately grouped as negative or positive for each of the three antigens (FIG. 4). Out of the 188 sera, 107 detected the 31 kDa OspA antigen, 39 detected the 22 kDa OspC and 82 identified the 29 kDa OspF protein by WB. Significantly higher ($p<0.0001$) MFI values were obtained in the multiplex assay for all three *B. burgdorferi* proteins using WB positive sera compared to those with negative WB results. In addition, ROC curves for the *B. burgdorferi* OspA, OspC and OspF antigens were generated using the WB results of the 188 sera as a 'relative gold standard' (FIG. 5). The ROC curves showed high agreement between the multiplex assay and WB results for OspA, OspC and OspF.

Interpretation of Multiplex Assay Results

To determine interpretation ranges for the *B. burgdorferi* OspA, OspC and OspF antigens in the multiplex assay, a likelihood analysis was performed. The analysis took into account that serological analyses almost always result in some false positive and false negative results when compared to a gold standard (Jacobson et al. 1996). This can be caused by the nature of some sera showing increased non-specific binding, by a suboptimal gold standard or by differences in the analytical sensitivity of the assays that are compared. Thus, a negative, an equivocal and a positive interpretation range was determined for each antigen. Table 5 shows the interpretation range, the likelihood ratio of a positive test (LR+) and the diagnostic sensitivity and specificity for the multiplex analysis of antibodies to each of the *B. burgdorferi* OspA, OspC and OspF antigens in canine serum. The diagnostic specificities of the OspA, OspC and OspF assays in the multiplex format were 90%, 89% and 86%, respectively. The diagnostic sensitivities were 83% (OspA), 62% (OspC) and 82% (OspF).

TABLE 5

Interpretation ranges of the fluorescent bead-based multiplex assay for antibodies to *B. burgdorferi* OspA, OspC and OspF in canine serum.

|  | Multiplex assay (MFI) | True positive (WBpos) | False positive (WBneg) | LR+ | Sensitivity (%) | 95% CI | Specificity (%) | 95% CI |
|---|---|---|---|---|---|---|---|---|
| OspA |  |  |  |  |  |  |  |  |
| Negative | <500 | 3/107 | 41/81 | 0.055 |  |  |  |  |
| Equivocal | ≥500 <1,500 | 15/107 | 32/81 | 0.35 |  |  |  |  |
| Positive | ≥1,500 | 89/107 | 8/81 | 8.40 | 83 | 75-90 | 90 | 82-96 |
| OspC |  |  |  |  |  |  |  |  |
| Negative | <250 | 3/39 | 65/149 | 0.18 |  |  |  |  |
| Equivocal | ≥250 <1,000 | 12/39 | 67/149 | 0.68 |  |  |  |  |
| Positive | ≥1,000 | 24/39 | 17/149 | 5.40 | 62 | 45-77 | 89 | 82-93 |
| OspF |  |  |  |  |  |  |  |  |
| Negative | <750 | 3/82 | 37/106 | 0.11 |  |  |  |  |
| Equivocal | ≥750 <1,500 | 12/82 | 56/106 | 0.28 |  |  |  |  |
| Positive | ≥1,500 | 67/82 | 15/106 | 5.75 | 82 | 72-89 | 86 | 78-92 |

It will be apparent from the foregoing that, in this Example, we demonstrate the development and validation of a new multiplex assay to detect serum antibodies to B. burgdorferi OspA, OspC and OspF antigens simultaneously. The multiplex assay combines the current testing procedures of ELISA and WB in one test and also distinguishes between individual B. burgdorferi antigens as markers for vaccination or infection. ELISA followed by WB is still considered the gold standard for detection of antibodies to B. burgdorferi. ELISAs performed on whole cell lysates of B. burgdorferi had high diagnostic sensitivity but rather low diagnostic specificity (Jacobson et al. 1996). False positive ELISA results using whole cell lysates were caused by reactions of serum antibodies with spirochete proteins that share a high homology with corresponding proteins of other bacteria, e.g. the flagellar protein of B. burgdorferi (Lindenmayer et al. 1990, Shin et al. 1993). That the multiplex assay developed here used novel recombinant proteins of B. burgdorferi reduced the possibility for cross-reactions in the new assay.

Here, we compared WB results for specific B. burgdorferi antigens to multiplex results for the corresponding OspA, OspC and OspF antigens. The ROC curve analysis indicated good to very good associations between the two tests. However, disagreements between WB and the multiplex assay were observed. One possible explanation for the disagreements could be that WB generally depends on the observer's subjective interpretation of whether a specific band is present or not. The interpretation of the WB can also be influenced by day-to-day variations in blot development. The analytical sensitivity of the WB (low µg/ml range) is less than that of ELISA (low ng/ml range) and much less than the analytical sensitivity of multiplex assays (low pg/ml range). Thus, it is likely that various sera with lower concentrations of antibodies to B. burgdorferi were not detected by WB but were identified by the multiplex assay.

Besides the increase in analytical sensitivity of multiplex assays compared to WB some bands on the blot can also be mis-interpreted. For example, B. burgdorferi expresses two proteins that appear at around 22 kDa on the WB, OspC and an additional protein of 22 kDa (Magnarelli et al. 2001). Because crude preparations of B. burgdorferi are generally used for WB, the analysis of antibodies to OspC can be complicated by the presence of antibodies to the 22 kDa protein in a sample. Consequently, the 22 kDa bands identified by WB might not always correspond to antibodies to OspC. This could explain the lower agreement that we observed between the bead-based OspC assay and WB results. Thus, the true diagnostic specificity and sensitivity for the OspC multiplex assay is likely higher than those calculated by comparison to the 22 kDa protein detected by WB. Overall, we concluded that WB can only be a 'relative gold standard' for validation of other assays detecting antibodies to B. burgdorferi.

Using a set of 188 canine serum samples, we observed a high discrepancy in the total numbers of WB positive samples for OspC (n=39) and OspF (n=82). This is in agreement with the differential expression of B. burgdorferi antigens and the resulting host antibody response discussed above. The samples originated from diagnostic field submissions and thus, the time of infection and/or vaccination of these dogs was not known. We observed that depending on the serum sample antibodies to either OspC or OspF or both could be detected by the multiplex assay suggesting that these outer surface protein detection patterns were indicative of different stages of infection with B. burgdorferi. Thus, differential antibody patterns to the OspC and OspF antigens is indicative of when the exposure to B. burgdorferi occurred in the dog. Such improved determination of the infection stage is likely to be valuable for treatment decisions and to predict treatment success.

Thus, the multiplex assay described in this Example for detection of antibodies to B. burgdorferi OspA, OspC and OspF antigens provides a quantitative, economic and sensitive alternative to determine antibodies in canine serum that are indicators of infection with B. burgdorferi and/or antibodies that resulted from vaccination.

EXAMPLE 2

This Example provides a description of one embodiment of the method demonstrating its enhanced utility for determining Lyme disease status in equines. The multiplex assay for horses uses OspA, OspC and OspF, as markers for vaccination and/or early or chronic infection as previously described for the canine Lyme assay in Example 1. In general, multiplex assays use the principle of simultaneous detection of soluble analytes in biological samples (Morgan et al. 2004, Prabhakar et al. 2005). They are based on fluorescent beads coupled with individual antigens which provide the matrix of the assay. Multiplex assays typically detect antibodies in the pg/ml range, while ELISA detect ng/ml and WB µg/ml concentrations (Kellar and Douglas 2003, Morgan et al. 2004, Wagner and Freer 2009). Thus, the new Lyme multiplex assay for horses is based on specific marker proteins for infection with or vaccination against B. burgdorferi and also likely has an advantage in situations when concentrations of antibodies are low such as early after infection or in cerebrospinal fluid samples from horses with neurological signs.

The following material and methods were used to obtain the results presented in this Example.

Recombinant B. Burgdorferi Proteins and Coupling to Fluorescent Beads

B. burgdorferi OspA, OspC and OspF antigens were expressed in E. coli and were coupled to fluorescent beads as described in Example 1. OspA was coupled to bead 33, OspC to bead 34, and OspF to bead 37. The coupling was performed according to the recommended protocol from the bead supplier.

Multiplex Assay

Multiplex analysis was performed as previously described for canine serum samples in Example 1 with the following changes: Equine serum samples were diluted at 1:400. For detection of serum antibodies a biotinylated goat anti-horse IgH(H+L) antibody (Jackson Immunoresearch Laboratories, West Grove, Pa.) was used at a dilution of 1:3000. All other reagents, buffers and incubation steps were identical to the procedure described before. The assay was analyzed in a Luminex IS 100 instrument (Luminex Corp.). The data were reported as median fluorescent intensities (MFI).

Horse Serum

Figure 6:
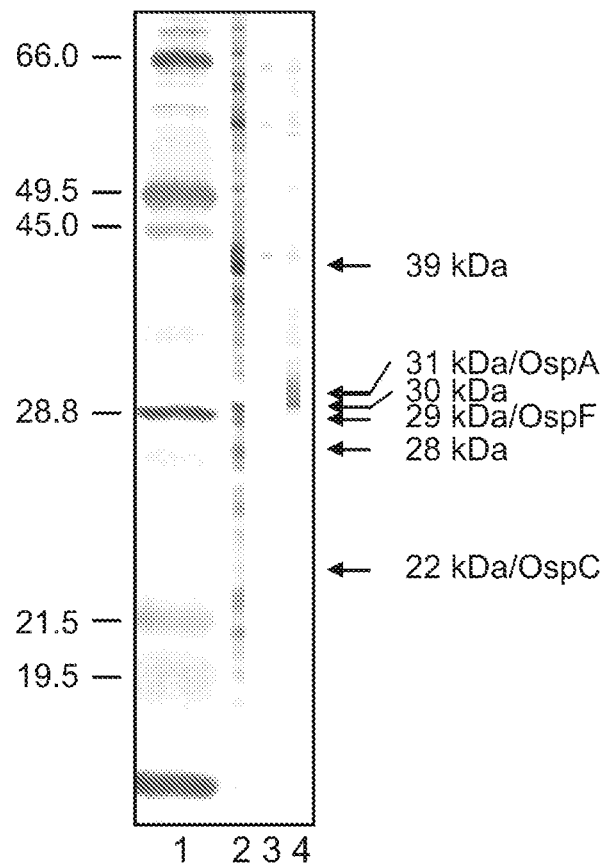
FIG. 6: Analysis of antibodies in equine serum for detection of *B. burgdorferi* proteins by Western blotting. A whole cell lysate of *B. burgdorferi* was separated by SDS-PAGE and proteins were transferred to nitrocellulose membranes by Western blotting. Lane (1) shows the molecular weight marker. The remaining lanes were stained with (2) serum from a horses infected with *B. burgdorferi*, (3) serum from a non-infected horse, or (4) serum from a horse that was vaccinated against Lyme disease. The sera from infected and vaccinated horses show characteristic detection pattern. Antibodies to OspC, OspF and also the 28, 30 and 39 kDa antigens are indicators of infection, while OspA is considered to be a marker for vaccinated horses.

All equine serum samples were submitted to the Animal Health Diagnostic Center at Cornell University for serological Lyme testing and were tested in a kinetic ELISA followed by WB to detect antibodies to B. burgdorferi. Both assays used whole cell lysates of B. burgdorferi and were performed as described previously (Chang et al. 2000a). Two sets of equine serum samples were analyzed for this approach:

First, 81 equine serum samples with available ELISA and WB results for antibodies to B. burgdorferi were used to establish the conditions of the bead-based assay for each of the antigens and for the comparison of singleplex and multiplex analyses. These 81 samples were selected to provide similar numbers of samples within the negative to high-positive interpretation ranges as identified by ELISA and WB and included sera from vaccinated and/or naturally infected horses. Second, a total of 562 equine serum samples that were not tested previously were evaluated for further multiplex assay validation. These samples were submitted to the Animal Health Diagnostic Center at Cornell University between July 2008 and June 2009. All samples were also analyzed for antibodies to *B. burgdorferi* antigens by WB. The presence (positive) or absence (negative) of serum antibodies to 31 kDa (OspA), 22 kDa (OspC) and 29 kDa (OspF) on the blots was determined blindly by an observer who was not aware of the multiplex assay results (FIG. 6).

Statistical Analysis

MFI values obtained from the first set of serum samples (n=81) were analyzed by singleplex and multiplex assay formats and were compared for each of the *B. burgdorferi* antigens by calculating Spearman rank correlations. Mann-Whitney tests were performed to compare differences in multiplex assay MFI values for samples that were either negative or positive for the respective antigen when tested by WB. The Mann-Whitney tests were run with Gaussian approximation, 2-sided, with 95% confidence intervals and using p<0.05 as cut-off for significance. The Spearman rank correlations and the Mann-Whitney tests were performed using the GraphPad Prism program, version 5.01.

For the second serum sample set (n=562), the WB results were used as a 'relative gold standard' (positive/negative) in a receiver operating characteristic (ROC) curve analysis and were compared to the multiplex MFI value. This analysis assumed that WB is indeed a true gold standard (i.e. 100% diagnostic sensitivity and specificity). A likelihood-ratio analysis was performed to define ranges of interpretation for antibodies to *B. burgdorferi* OspA, OspC and OspF antigens and diagnostic sensitivities and specificities of the multiplex assay. ROC curves and likelihood analyses were performed separately for each antigen. The ROC curves were generated using the MedCalc program, version 11.2.0.0 2010, MedCalc Software, Broekstraat 52, 9030 Mariakerke. The likelihood analysis was performed using Statistix 9.0, 2008, Analytical Software, Tallahassee, Fla., USA.

The second serum sample set was also used for a Bayesian statistical approach which can be used for the analysis of assay performance if a true gold standard is not available (Wang et al. 2007). For Lyme antibody testing the WB can only be considered as a 'relative gold standard' because of its poor analytical sensitivity and its subjective component in analyzing whether a specific band is present or not (Wagner et al. 2011). The data were analyzed using a Bayesian model to identify diagnostic specificity, sensitivity and positive cut-off values for both tests, the new Lyme multiplex assay and WB.

The Bayesian approach required two groups with different prevalence of disease indicators otherwise the Bayesian model that was used to estimate parameters becomes non-identifiable (Wang et al. 2006, Wang et al. 2007). Thus, the serum samples were artificially split into two groups. All samples collected between July and December 2008 (n=408) were assigned into group 1, all samples collected between January and June 2009 (n=156) were in group 2. This separation was based on the assumption that the prevalence of antibodies to *B. burgdorferi*, as indicators of Lyme disease, is higher from July to December than during the first six months of the year. The analysis showed that this assumption was true for antibodies to OspC and OspF and the analysis was performed. For OspA, the prevalence between the two groups was similarly low and the Bayesian approach could not be used for the OspA assay.

Results

Development of an Equine Multiplex Assay for Detection of Antibodies to *B. Burgdorferi*

Figure 7:
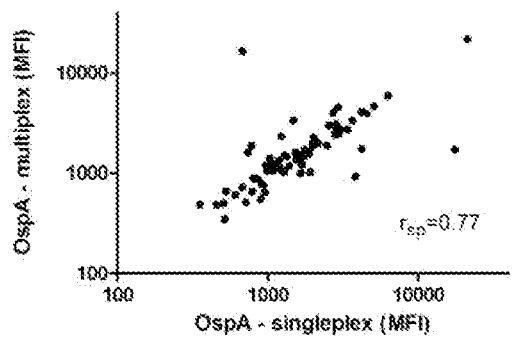
FIG. 7: Comparison of singleplex and multiplex results for antibodies to the OspA, OspC and OspF antigens of *B. burgdorferi* detected in 81 equine serum samples. Multiplex assay results are expressed as median fluorescence intensities (MFI). Spearman rank correlations ($r_{sp}$) were calculated for each of the comparisons.
Figure 7:
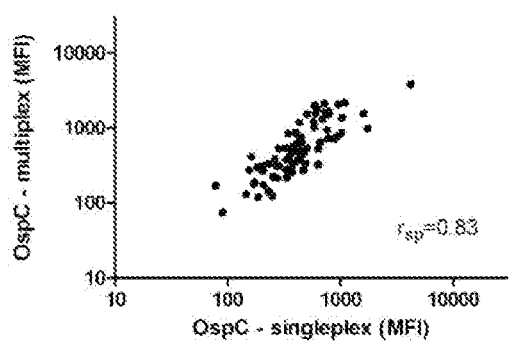
Figure 7:
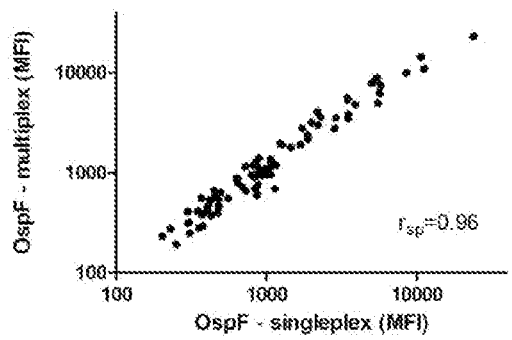

A total of 81 pretested horse sera with or without antibodies to *B. burgdorferi* were used to establish the conditions of the fluorescent bead-based assays. Beads were coupled with recombinant OspA, OspC or OspF antigens of *B. burgdorferi*. The measurement of serum antibodies to these antigens was compared by running the assays on individual beads (singleplex) and also by multiplex analysis (FIG. 7). Multiplex and singleplex analysis results for antibodies to *B. burgdorferi* highly correlated. Spearman rank values for the individual antigen comparisons were 0.77, 0.83 and 0.96 for OspA, OspC and OspF, respectively. The background values for the multiplex assay were <10 MFI for OspA and OspC and <100 MFI for OspF (Table 6). The 81 serum samples resulted in MFIs between 347-21650 for OspA, 75-3842 for OspC, and 192-23209 for OspF confirming the wide dynamic range of the Lyme multiplex assay.

TABLE 6

Median fluorescence intensities (MFI) values (median, range) and background values of a fluorescent bead-based multiplex assay for antibodies to *B. burgdorferi* OspA, OspC and OspF antigens in equine serum (n = 562).

| | Background[a] | WB negative | WB positive |
| --- | --- | --- | --- |
| OspA | 3.5 (2.5-8.0) | 866 (160-20, 451) | 2317 (206-27, 471) |
| OspC | 4.7 (3.0-8.0) | 439 (59-4702) | 1106 (128-9261) |
| OspF | 85.0 (62.5-96.5) | 848 (209-14,550) | 2560 (217-25,961) |

Figure 8:
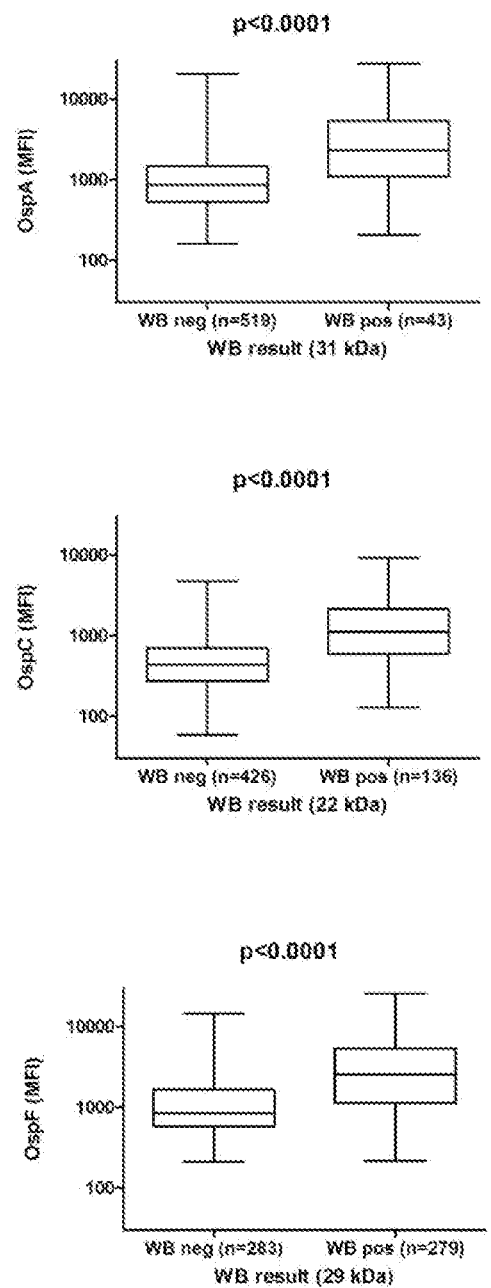
FIG. 8: Western blot (WB) and multiplex results (MFI) for antibodies to the OspA, OspC and OspF antigens of *B. burgdorferi* were compared in 562 equine serum samples. A clear increase in MFI values was observed for all three bead-based assays by using WB positive sera compared to WB negative samples indicated by p-values of <0.0001.

[a]Background values were obtained from 18 separate runs of the multiplex assay without serum
WB = Western blot Validation of the Equine Lyme Multiplex Assay The validation of the multiplex assay for antibodies to OspA, OspC and OspF was performed by comparing multiplex results to the corresponding results obtained by WB for a total of 562 horse sera. By WB, antibodies to OspC and OspF can be detected in horses that were infected with *B. burgdorferi* after tick bites. Antibodies to OspA are considered to develop after vaccination against Lyme disease (FIG. 6). The MFI values obtained by the multiplex assay were compared to WB negative and positive serum samples. This showed a clear increase of MFI values in WB positive samples compared to WB negative samples for each of the individual antigens (FIG. 8). Despite these clear differences in the overall MFI values, the analysis also showed an overlap between the MFI values of WB negative and positive samples (Table 6) which required further evaluation of the multiplex assays cut-off values by various statistical approaches.

Analysis Using WB as a 'Relative Gold Standard'

WB can only be considered as a 'relative gold standard' because of its relatively poor analytical sensitivity and the subjective component involved in WB evaluation. Nevertheless, ROC curves were created by comparing the multiplex assay results for individual OspA, OspC or OspF assays to the presence of the corresponding band on WB or not. The areas under the ROC curve were 0.765 for OspA, 0.773 for OspC and 0.738 for OspF. Because of the overlapping MFI values of WB negative and WB positive samples (FIG. 8), we also performed a likelihood-ratio analysis to establish three interpretation ranges, negative, equivocal and positive, for each of the bead-based assays. Diagnostic sensitivity and specificity values were also calculated based on positive cut-off values of the likelihood analysis (Table 7).

TABLE 7

Interpretation ranges of the fluorescent bead-based multiplex assay for antibodies to *B. burgdorferi* OspA, OspC and OspF in equine serum.

| | Multiplex assay (MFI) | True positive % (WBpos) | False positive % (WBneg) | LR+ | Sensitivity (%) | Specificity (%) |
|---|---|---|---|---|---|---|
| OspA | | | | | | |
| Negative | <1000 | 18.6 | 57.6 | 0.323 | | |
| Equivocal | ≥1000-2000 | 32.6 | 27.4 | 1.19 | | |
| Positive | >2000 | 48.8 | 15.0 | 3.25 | 49 | 85 |
| OspC | | | | | | |
| Negative | <500 | 19.1 | 59.2 | 0.323 | | |
| Equivocal | ≥500-1000 | 25.0 | 26.5 | 0.943 | | |
| Positive | >1000 | 55.9 | 14.3 | 3.91 | 56 | 86 |
| OspF | | | | | | |
| Negative | <750 | 15.4 | 42.4 | 0.363 | | |
| Equivocal | ≥750-1250 | 12.5 | 24.4 | 0.512 | | |
| Positive | >1250 | 72.0 | 33.2 | 2.17 | 72 | 67 |

LR = likelihood ratio

Assay Validation in the Absence of a True Gold Standard Using a Bayesian Model

To take into account that WB very likely also resulted in several interpretation mistakes we performed another analysis using a Bayesian approach that estimates diagnostic sensitivities and specificities for both tests that are compared. The analysis required two experimental groups with different prevalence. The data were obtained from sample submissions within one year and they were artificially split into sera submitted between July to December (group 1) and samples submitted between January to June (group 2) assuming a higher Lyme disease prevalence in group 1. The analysis confirmed that the prevalence of antibodies to *B. burgdorferi* was higher in group 1 for the two infection markers OspC and OspF, but not for the vaccination marker OspA. Thus, the model could only be run on results for antibodies to OspC and OspF and compared the bead-based assay and the WB as two independent tests, none of them being a gold standard (Table 8). For antibodies to OspC, the bead-based assay resulted in a diagnostic sensitivity of 80% and a diagnostic specificity of 79%. The OspC WB had a sensitivity of only 72% and a specificity of 92%. For antibodies to OspF, the sensitivity was 86% and the specificity 69% for the bead-based assay. The OspF WB had a sensitivity of 80% and a specificity of 77%. The Bayesian analysis suggested that a greater number of false negatives was obtained by WB than by multiplex analysis. The higher specificity values of the WB were indicative of low numbers of false positives detected by this test. The cut-off values for the OspC and OspF bead-based assays were 813 and 1270 MFI, respectively, which falls into the equivocal (OspC) or very low positive (OspF) interpretation ranges as defined by likelihood analysis (Tables 7 and 8).

TABLE 8

Bayesian statistical analysis comparing the new multiplex assay and Western blotting (WB) for antibodies to OspC or OspF of *B. burgdorferi*.

| *B. burgdorferi* outer surface protein | Test | Sensitivity (%) | Specificity (%) | Optimal cut-off value (multiplex) |
|---|---|---|---|---|
| OspC | Multiplex | 80 (68-90) | 79 (73-85) | 813 |
| | WB | 72 (55-89) | 92 (88-96) | NA |
| OspF | Multiplex | 86 (77-93) | 69 (60-79) | 1270 |
| | WB | 80 (70-89) | 77 (69, 88) | NA |

Diagnostic assay sensitivity and specificity are expressed in terms of optimal values with 95% credible interval level.
NA = not applicable because WB is a qualitative test and thus has no cut-off values It will be apparent from the foregoing that in this Example we used *E. coli-expressed* OspA, OspC and OspF antigens of *B. burgdorferi* to develop a new multiplex assay for detection of antibodies indicative for Lyme disease. A major challenge in the validation of the new multiplex assay was the absence of a true gold standard to establish cut-off values, interpretation ranges, and diagnostic sensitivity and specificity values. WB for detection of antibodies to *B. burgdorferi* is considered a confirmatory test and the best available standard for serological Lyme diagnostic. Using WB as a gold standard for test validation assumes 100% diagnostic sensitivity and specificity for this method. Based on this fact a new test can never be better than the existing test by using conventional gold standard methods. However, WB is a qualitative test and has limitations in respect to its analytical sensitivity, day-to-day variations in blot development and its subjective evaluation that can result in misinterpretation of bands even by experienced evaluators (see Example 1). Although the interpretation of WB results is straight forward for samples with very high antibody titers or in experimentally infected horses kept in isolation, it can be more difficult in clinical situations when the infection history is unknown and/or for sera containing lower antibody levels to *B. burgdorferi*. These characteristics of WB evaluation, together with the expected differences in analytical sensitivities between WB and multiplex technology, caused us to explore different statistical approaches to validate the new Lyme multiplex assay. The conventional ROC-curve and likelihood-ratio analyses were performed under the assumption that WB is a true gold standard, i.e. 100% accurate. The Bayesian model approach can analyze diagnostic assays in the absence of a gold standard (Wang et al. 2006, Wang et al. 2007) and compared WB and multiplex assay as equal tests. Therefore, the analysis resulted in diagnostic sensitivity and specificity data for both assays. Although all these assumptions may not be entirely true because the two tests obviously widely differ in their analytical sensitivities, the Bayesian analyses allowed us to estimate the diagnostic sensitivity and specificity of the new multiplex assay more accurately by taking into account that WB is not a true gold standard, i.e. not 100% correct. Consequently, diagnostic sensitivity and specificity values for the Lyme multiplex assay were higher in the Bayesian method than in the 'relative gold standard' approach. The conventional gold standard analysis suggested values of 56% and 72% for sensitivity and 86% and 67% for specificity of the OspC and OspF bead-based assays, respectively. Based on the discussion on WB above, these values likely underestimated the true specificity and sensitivity of the multiplex assay. The Bayesian model confirmed the latter statement on WB and calculated a lower diagnostic sensitivity but higher diagnostic specificity for WB compared to the OspC and OspF bead-based assays. The Bayesian analysis resulted in diagnostic sensitivities of 80% for OspC and 86% for OspF in the multiplex assay compared to 72% and 80%, respectively, by WB. The diagnostic sensitivity values of the multiplex assay are clearly improved compared to the conventional gold standard approach and better reflect the real diagnostic sensitivity values because of the improved analytical sensitivity of antibody detection by multiplex analysis (pg/ml) compared to WB (µg/ml). The diagnostic specificity of the multiplex assay using Bayesian analysis was 79% for OspC (WB 92%) and 69% for OspF (WB 77%) which is also improved for OspF and slightly lower for OspC compared to the gold standard based calculations. One reason for the difference in the specificity values for the OspC assay is the greater difference in the cut-off values for OspC by the two statistical methods applying a lower cut-off value for OspC in the calculation of the Bayesian approach than for the gold standard analysis.

Gold standard and Bayesian analyses were also used to establish cut-off values for antibodies to OspC and OspF. For OspC, the likelihood-ratio analysis suggested a positive cut-off value of >1000 MFI and the Bayesian approach identified an even lower cut-off value of 813 MFI. For OspF, the likelihood analysis found >1250 MFI as the optimal positive cut-off which was almost identical to the 1270 MFI cut-off in the Bayesian approach. Considering the wide dynamic range of the multiplex assay that resulted for our sample set in MFI values of almost 10.000 for OspC and >25.000 for OspF, the suggested cut-off values confirmed the wide dynamic range of this test which allows a detailed quantitative analysis of antibodies to *B. burgdorferi* in equine serum. The wide dynamic quantification range is a considerable advantage of the multiplex approach compared to currently existing quantitative tests such as ELISAs which have a rather narrow linear quantification range (Wagner and Freer 2009). In our experience, the most considerable advantage of the increased linear dynamic range is that sera can be used in a single dilution in the multiplex assay and results almost always fit into the linear quantification range of the assay with the exception of a very few results that still fall into the upper plateau of the assay, i.e. these sera contain very high concentrations of antibodies to the respective *B. burgdorferi* Osp antigen.

Current conventional Lyme ELISAs are often based on whole *B. burgdorferi* lysates and do not distinguish between infection and vaccination. These assays bare the risk of non-specific cross-reactivity to common bacterial components in the lysate mixture (Lindenmayer et al. 1990, Shin et al. 1993, Jacobson et al. 1996). Thus if positive, these assays need a second confirmatory test, such as a qualitative WB. In situations where quantification of antibodies is required, for example to determine the success of antibiotic treatment in horses with Lyme disease, testing always required two tests: first, a quantitative ELISA to confirm the antibody decrease and a second WB test to confirm that the decrease was specific for antibodies indicative for Lyme disease. Other on-side (stick-based tests) or ELISA based tests such as the determination of antibodies to C6 were found to correlate well with infection of horses with the Lyme pathogen (Johnson et al. 2008, Hansen et al. 2010, Maurizi et al. 2010). However, it did not appear that antibodies to C6 were detected earlier or declined more rapidly than antibodies detected by a conventional *B. burgdorferi* ELISA (Johnson et al. 2008).

Both, WB and the new multiplex Lyme assay can distinguish between antibodies that resulted from natural infection with *B. burgdorferi* and those developed after vaccination. The latter response is characterized by high values for antibodies to the OspA antigen of *B. burgdorferi* as frequently described in humans, laboratory rodents, dogs (Fikrig et al. 1990, Schaible et al. 1990, Jacobson et al. 1996, Wittenbrink et al. 1996, Wieneke et al. 2000, Töpfer and Straubinger 2007) and also in horses (Chang et al. 2000b). Approved Lyme vaccines for use in horses currently do not exist. Thus, vaccines for dogs are sometimes used for horses that are housed in areas where Lyme disease is endemic (Divers 2009). The absence of an approved vaccine explains the overall low numbers of OspA positive equine sera (43 out of 562) in our sample set. The Bayesian model could not be performed on this data set for antibodies to OspA because the prevalence of antibodies to OspA between the two groups was similar. This is not surprising because vaccination can be performed at any time and does not necessarily follow seasonal peaks like infection with *B. burgdorferi* which depends on the occurrence of infected ticks in the environment. For vaccinated horses housed in endemic areas the quantitative evaluation of vaccination titers is valuable information that can direct the decision to re-vaccinate or not for preventing Lyme disease in these horses. The new multiplex assay is the first available test that quantifies antibody responses to the vaccination marker OspA and is also able to distinguish host responses to vaccination from those to infection. Vaccine responses can either be characterized by antibodies to OspA only or to OspA and OspC depending on the vaccine used. OspF is not included into currently available vaccines and thus remains a marker for infection even if the horse was vaccinated.

In summary, the use of two statistical approaches to validate the new Lyme multiplex assay for horses resulted in similar cut-off and diagnostic sensitivity and specificity values for the infection markers OspC and OspF. The analysis also resulted in the first diagnostic sensitivity and specificity evaluation of WB, the traditional gold standard for the analysis of antibodies to *B. burgdorferi*. The overall performance of the multiplex assay showed that it is a valuable test with likely improved analytical and diagnostic sensitivity compared to WB. The new Lyme multiplex assay for horses provides a valuable, quick, sensitive and quantitative tool for the detection of antibodies indicative for infection with and/or vaccination against Lyme disease in horses.

While the invention has been described through illustrative examples, routine modifications will be apparent to those skilled in the art, which modifications are intended to be within the scope of the invention.

We claim:

1. A composition comprising a combination of *Borrelia burgdorferi* (*B. burgdorferi*) outer surface proteins, wherein the proteins are the only *B. burgdorferi* proteins in the composition, wherein the proteins comprise the sequences of SEQ ID NO: 15, SEQ ID NO: 17, and SEQ ID NO: 19, wherein the proteins are covalently attached to a solid matrix, wherein the composition is suitable for use in determining vaccination against *B. burgdorferi*, early *B. burgdorferi* infection, intermediate *B. burgdorferi* infection and late *B. burgdorferi* infection, wherein the early infection is 2 to 6 weeks old, wherein the intermediate infection is from 6 weeks to 5 months old, and wherein the chronic infection is present for more than 5 months.

2. The composition of claim 1, wherein the solid matrix comprises fluorescent beads.

3. The composition of claim 1, wherein the solid matrix is present in a lateral flow device.

* * * * *

SEQUENCE LISTING

<160> NUMBER OF SEQ ID NOS: 19

<210> SEQ ID NO 1
<211> LENGTH: 273
<212> TYPE: PRT
<213> ORGANISM: B. burgdorferi

<400> SEQUENCE: 1

```
Met Lys Lys Tyr Leu Leu Gly Ile Gly Leu Ile Ala Leu Ile Ala
1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Leu Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 2
<211> LENGTH: 211
<212> TYPE: PRT
<213> ORGANISM: B. burgdorferi

<400> SEQUENCE: 2

Met Lys Lys Asn Thr Leu Ser Ala Ile Leu Met Thr Leu Phe Leu Phe
1               5                  10                  15

Ile Ser Cys Asn Asn Ser Gly Lys Asp Gly Asn Thr Ser Ala Asn Ser
                20                  25                  30

Ala Asp Glu Ser Val Lys Gly Pro Asn Leu Thr Glu Ile Ser Lys Lys
            35                  40                  45

Ile Thr Asp Ser Asn Ala Val Leu Leu Ala Val Lys Glu Val Glu Ala
        50                  55                  60

Leu Leu Ser Ser Ile Asp Glu Leu Ala Lys Ala Ile Gly Lys Lys Ile
65                  70                  75                  80

Lys Asn Asp Gly Ser Leu Asp Asn Glu Ala Asn Arg Asn Glu Ser Leu
                85                  90                  95
```

```
Leu Ala Gly Ala Tyr Thr Ile Ser Thr Leu Ile Thr Gln Lys Leu Ser
                100                 105                 110

Lys Leu Asn Gly Ser Glu Gly Leu Lys Glu Lys Ile Ala Ala Ala Lys
        115                 120                 125

Lys Cys Ser Glu Glu Phe Ser Thr Lys Leu Lys Asp Asn His Ala Gln
    130                 135                 140

Leu Gly Ile Gln Gly Val Thr Asp Glu Asn Ala Lys Lys Ala Ile Leu
145                 150                 155                 160

Lys Ala Asn Ala Ala Gly Lys Asp Lys Gly Val Glu Glu Leu Glu Lys
                165                 170                 175

Leu Ser Gly Ser Leu Glu Ser Leu Ser Lys Ala Ala Lys Glu Met Leu
                180                 185                 190

Ala Asn Ser Val Lys Glu Leu Thr Ser Pro Val Val Ala Glu Ser Pro
            195                 200                 205

Lys Lys Pro
        210

<210> SEQ ID NO 3
<211> LENGTH: 227
<212> TYPE: PRT
<213> ORGANISM: B. burgdorferi

<400> SEQUENCE: 3

Met Asn Lys Lys Met Phe Ile Ile Cys Ala Val Phe Ala Leu Ile Ile
1               5                   10                  15

Ser Cys Lys Asn Tyr Ala Thr Ser Lys Asp Leu Glu Gly Ala Val Gln
            20                  25                  30

Asp Leu Glu Ser Ser Glu Gln Asn Val Lys Lys Thr Glu Gln Glu Ile
        35                  40                  45

Lys Lys Gln Val Glu Gly Phe Leu Glu Ile Leu Glu Thr Lys Asp Leu
50                  55                  60

Asn Lys Leu Asp Thr Lys Glu Ile Glu Lys Arg Ile Gln Glu Leu Lys
65                  70                  75                  80

Glu Lys Ile Glu Lys Leu Asp Ser Lys Lys Thr Ser Ile Glu Thr Tyr
                85                  90                  95

Ser Glu Tyr Glu Glu Lys Leu Lys Gln Ile Lys Glu Lys Leu Lys Gly
            100                 105                 110

Lys Ala Asp Leu Glu Asp Lys Leu Lys Gly Leu Glu Asp Ser Leu Lys
        115                 120                 125

Lys Lys Lys Glu Glu Arg Lys Lys Ala Leu Glu Asp Ala Lys Lys Lys
    130                 135                 140

Phe Glu Glu Phe Lys Gly Gln Val Gly Ser Ala Thr Gly Val Thr Thr
145                 150                 155                 160

Gly His Arg Ala Gly Asn Gln Gly Ser Ile Gly Ala Gln Ala Trp Gln
                165                 170                 175

Cys Ala Asn Ser Leu Gly Leu Gly Val Ser Tyr Ser Ser Ser Thr Gly
            180                 185                 190

Thr Asp Ser Asn Glu Leu Ala Asn Lys Val Ile Asp Asp Ser Ile Lys
        195                 200                 205

Lys Ile Asp Glu Glu Leu Lys Asn Thr Ile Glu Asn Asn Gly Glu Val
    210                 215                 220

Lys Lys Glu
225

<210> SEQ ID NO 4
```

```
<211> LENGTH: 29
<212> TYPE: DNA
<213> ORGANISM: B. burgdorferi

<400> SEQUENCE: 4
cgcggatcca tgaaaaaata tttattggg                                    29

<210> SEQ ID NO 5
<211> LENGTH: 32
<212> TYPE: DNA
<213> ORGANISM: B. burgdorferi

<400> SEQUENCE: 5
ggcggtacct caagttgaag tgcctgaatt cc                                32

<210> SEQ ID NO 6
<211> LENGTH: 31
<212> TYPE: DNA
<213> ORGANISM: B. burgdorferi

<400> SEQUENCE: 6
cgcggatcct cttgtaataa ttcagggaaa g                                 31

<210> SEQ ID NO 7
<211> LENGTH: 33
<212> TYPE: DNA
<213> ORGANISM: B. burgdorferi

<400> SEQUENCE: 7
ggcggtacct caaggttttt ttggactttc tgc                               33

<210> SEQ ID NO 8
<211> LENGTH: 29
<212> TYPE: DNA
<213> ORGANISM: B. burgdorferi

<400> SEQUENCE: 8
cgcggatccg agacgaaaga tttgaataa                                    29

<210> SEQ ID NO 9
<211> LENGTH: 30
<212> TYPE: DNA
<213> ORGANISM: B. burgdorferi

<400> SEQUENCE: 9
ggcggtacct tattcttttt tgacttctcc                                   30

<210> SEQ ID NO 10
<211> LENGTH: 23
<212> TYPE: DNA
<213> ORGANISM: B. burgdorferi

<400> SEQUENCE: 10
atgaaaaaga atacattaag tgc                                          23

<210> SEQ ID NO 11
<211> LENGTH: 27
<212> TYPE: DNA
<213> ORGANISM: B. burgdorferi

<400> SEQUENCE: 11
ttaaggtttt tttggactttt ctgccac                                     27
```

<210> SEQ ID NO 12
<211> LENGTH: 29
<212> TYPE: DNA
<213> ORGANISM: B. burgdorferi

<400> SEQUENCE: 12
atgaataaaa aaatgtttat tatttgtgc					29

<210> SEQ ID NO 13
<211> LENGTH: 21
<212> TYPE: DNA
<213> ORGANISM: B. burgdorferi

<400> SEQUENCE: 13
ttattctttt ttgacttctc c						21

<210> SEQ ID NO 14
<211> LENGTH: 822
<212> TYPE: DNA
<213> ORGANISM: B. burgdorferi

<400> SEQUENCE: 14
atgaaaaaat atttattggg aataggtcta atattagcct taatagcatg taagcaaaat		60 gttagcagcc ttgacgagaa aaacagcgtt tcagtagatt tgcctggtga atgaaagtt		120 cttgtaagca agaaaaaaa caaagacggc aagtacgatc taattgcaac agtagacaag		180 cttgagctta aggaacttc tgataaaaac aatggatctg gagtacttga aggcgtaaaa		240 gctgacaaaa gtaaagtaaa attaacaatt tctgacgatc taggtcaaac cacacttgaa		300 gttttcaaag aagatggcaa acactagta tcaaaaaaag taacttccaa agacaagtca		360 tcaacagaag aaaaattcaa tgaaaaaggt gaagtatctg aaaaaataat aacaagagca		420 gacggaacca gacttgaata cacaggaatt aaaagcgatg gatctggaaa agctaaagag		480 gttttaaaag ctatgttct tgaaggaact ctaactgctg aaaaaacaac attggtggtt		540 aaagaaggaa ctgttacttt aagcaaaaat atttcaaaat ctggggaagt tttagttgaa		600 cttaatgaca ctgacagtag tgctgctact aaaaaaactg cagcttggaa ttcgggcact		660 tcaactttaa caattactgt aaacagtaaa aaaactaaag accttgtgtt tacaaaagaa		720 aacacaatta cagtacaaca atacgactca aatggcacca aattagaggg gtcagcagtt		780 gaaattacaa aacttgatga aattaaaaac gctttaaat aa				822

<210> SEQ ID NO 15
<211> LENGTH: 222
<212> TYPE: PRT
<213> ORGANISM: B. burgdorferi

<400> SEQUENCE: 15

Met Lys Lys Tyr Leu Leu Gly Ile Gly Leu Ile Leu Ala Leu Ile Ala
1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln

```
                    85                  90                  95
Thr Thr Leu Glu Val Phe Lys Glu Asp Gly Lys Thr Leu Val Ser Lys
            100                 105                 110

Lys Val Thr Ser Lys Asp Lys Ser Thr Glu Glu Lys Phe Asn Glu
        115                 120                 125

Lys Gly Glu Val Ser Glu Lys Ile Ile Thr Arg Ala Asp Gly Thr Arg
        130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Leu Val Glu Leu Asn Asp Thr Asp Ser Ser Ala
            195                 200                 205

Ala Thr Lys Lys Thr Ala Ala Trp Asn Ser Gly Thr Ser Thr
        210                 215                 220

<210> SEQ ID NO 16
<211> LENGTH: 636
<212> TYPE: DNA
<213> ORGANISM: B. burgdorferi

<400> SEQUENCE: 16
atgaaaaaga atacattaag tgcaatatta atgactttat ttttatttat atcttgtaat     60
aattcaggga agatgggaa tacatctgca aattctgctg atgagtctgt taaagggcct    120
aatcttacag aaataagtaa aaaaattacg gattctaatg cggttttact tgctgtgaaa    180
gaggttgaag cgttgctgtc atctatagat gagcttgcta agctattgg taaaaaata     240 aaaaacgatg gtagtttaga taatgaagca atcgcaacg agtcattgtt agcaggagct    300
tatacaatat caaccttaat aacacaaaaa ttaagtaaat taaacggatc agaaggttta    360
aaggaaaaga ttgccgcagc taagaaatgc tctgaagagt ttagtactaa actaaaagat    420
aatcatgcac agcttggtat acagggcgtt actgatgaaa atgcaaaaaa agctatttta    480
aaagcaaatg cagcgggtaa agataagggc gttgaagaac ttgaaaagtt gtccggatca    540
ttagaaagct atcaaaagc agctaaagag atgcttgcta attcagttaa agagcttaca    600
agccctgttg tggcagaaag tccaaaaaaa ccttaa                              636

<210> SEQ ID NO 17
<211> LENGTH: 194
<212> TYPE: PRT
<213> ORGANISM: B. burgdorferi

<400> SEQUENCE: 17

Ser Cys Asn Asn Ser Gly Lys Asp Gly Asn Thr Ser Ala Asn Ser Ala
1               5                   10                  15

Asp Glu Ser Val Lys Gly Pro Asn Leu Thr Glu Ile Ser Lys Lys Ile
            20                  25                  30

Thr Asp Ser Asn Ala Val Leu Leu Ala Val Lys Glu Val Glu Ala Leu
        35                  40                  45

Leu Ser Ser Ile Asp Glu Leu Ala Lys Ala Ile Gly Lys Lys Ile Lys
    50                  55                  60

Asn Asp Gly Ser Leu Asp Asn Glu Ala Asn Arg Asn Glu Ser Leu Leu
65                  70                  75                  80
```

```
Ala Gly Ala Tyr Thr Ile Ser Thr Leu Ile Thr Gln Lys Leu Ser Lys
                85                  90                  95

Leu Asn Gly Ser Glu Gly Leu Lys Glu Lys Ile Ala Ala Lys Lys
            100                 105                 110

Cys Ser Glu Glu Phe Ser Thr Lys Leu Lys Asp Asn His Ala Gln Leu
            115                 120                 125

Gly Ile Gln Gly Val Thr Asp Glu Asn Ala Lys Lys Ala Ile Leu Lys
        130                 135                 140

Ala Asn Ala Ala Gly Lys Asp Lys Gly Val Glu Leu Glu Lys Leu
145                 150                 155                 160

Ser Gly Ser Leu Glu Ser Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro

<210> SEQ ID NO 18
<211> LENGTH: 684
<212> TYPE: DNA
<213> ORGANISM: B. burgdorferi

<400> SEQUENCE: 18
atgaataaaa aaatgtttat tatttgtgct gttttttgcgt tgataatttc ttgcaagaat      60
tatgcaacta gtaaagattt agaaggggca gtgcaagatt tagaaagttc agaacaaaat     120
gtaaaaaaaa cagaacaaga gataaaaaaa caagttgaag gattttttaga aattctagag    180 acgaaagatt tgaataaatt ggatacaaaa gagattgaaa aacgaattca agaattaaag    240
gaaaaaatag aaaaattaga ttctaaaaaa acttctattg aaacatattc tgagtatgaa    300
gaaaaactaa acaaataaa agaaaaattg aaaggaaagg cagatcttga agataaatta    360
aagggacttg aagatagctt aaaaagaaa aagaggaaa gaaaaaaagc tttagaagat    420
gctaagaaga aatttgaaga gtttaaagga caagttggat ccgcgactgg agtaactacc    480
gggcatagag ctggaaatca aggtagtatt ggggcacaag cttggcagtg tgctaatagt    540
ttggggttgg gtgtaagtta ttctagtagt actggtactg atagcaatga attggcaaac    600
aaagttatag atgattcaat taaaagagtt gatgaagagc ttaaaaatac tatagaaaat    660
aatggagaag tcaaaaaaga ataa                                            684

<210> SEQ ID NO 19
<211> LENGTH: 168
<212> TYPE: PRT
<213> ORGANISM: B. burgdorferi

<400> SEQUENCE: 19

Glu Thr Lys Asp Leu Asn Lys Leu Asp Thr Lys Glu Ile Glu Lys Arg
1               5                   10                  15

Ile Gln Glu Leu Lys Glu Lys Ile Glu Lys Leu Asp Ser Lys Lys Thr
            20                  25                  30

Ser Ile Glu Thr Tyr Ser Glu Tyr Glu Glu Lys Leu Lys Gln Ile Lys
        35                  40                  45

Glu Lys Leu Lys Gly Lys Ala Asp Leu Glu Asp Lys Leu Lys Gly Leu
    50                  55                  60

Glu Asp Ser Leu Lys Lys Lys Glu Glu Arg Lys Lys Ala Leu Glu
65                  70                  75                  80

Asp Ala Lys Lys Lys Phe Glu Glu Phe Lys Gly Gln Val Gly Ser Ala
```

-continued

```
                     85                    90                    95
Thr Gly Val Thr Thr Gly His Arg Ala Gly Asn Gln Gly Ser Ile Gly
                100               105               110

Ala Gln Ala Trp Gln Cys Ala Asn Ser Leu Gly Leu Gly Val Ser Tyr
        115               120               125

Ser Ser Ser Thr Gly Thr Asp Ser Asn Glu Leu Ala Asn Lys Val Ile
        130               135               140

Asp Asp Ser Ile Lys Lys Ile Asp Glu Glu Leu Lys Asn Thr Ile Glu
145               150               155                   160

Asn Asn Gly Glu Val Lys Lys Glu
                165
```